United States Patent
Sendai et al.

(10) Patent No.: US 6,747,281 B2
(45) Date of Patent: Jun. 8, 2004

(54) FLOURESCENT—LIGHT IMAGE DISPLAY METHOD AND APPARATUS THEREFOR

(75) Inventors: Tomonari Sendai, Kaisei-machi (JP); Kazuhiro Tsujita, Kaisei-machi (JP); Yukihiko Nakajima, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 216 days.

(21) Appl. No.: 09/919,853

(22) Filed: Aug. 2, 2001

(65) Prior Publication Data

US 2002/0014595 A1 Feb. 7, 2002

(30) Foreign Application Priority Data

Aug. 2, 2000 (JP) .......................................... 2000-234225

(51) Int. Cl.[7] .............................................. G01N 21/64
(52) U.S. Cl. ..................................... 250/458.1; 600/317
(58) Field of Search ........................ 600/317; 250/458.1, 250/459.1, 461.1, 461.2

(56) References Cited

U.S. PATENT DOCUMENTS 5,334,841 A * 8/1994 Graessle et al. ......... 250/458.1
6,070,096 A * 5/2000 Hayashi .................... 250/458.1
6,462,770 B1 * 10/2002 Cline et al. .................... 348/65

* cited by examiner

Primary Examiner—Constantine Hannaher
(74) Attorney, Agent, or Firm—Sughrue Mion, PLLC

(57) ABSTRACT

According to a method of and apparatus for displaying as an autofluorescent-light image emitted from a target subject upon the irradiation thereof by a excitation light, even for cases in which a malfunction of the apparatus occurs that prevents an operator from obtaining a desired image, a standard-image is displayed so as to enable an operator to safely and expediently remove the insertion portion of the endoscope from the body of a patient, whereby the safety of the patient can be ensured. When an irregularity in the temperature of one of the light sources, the operation of one of the drive apparatus, or other cause of an operational irregularity occurring in of one of the light sources is detected by the semiconductor-laser temperature detecting means, the reference-light source temperature detecting means, or the emission-output detecting means, in response to a detection signal thereof, the standard-image display mode is switched to automatically.

22 Claims, 12 Drawing Sheets

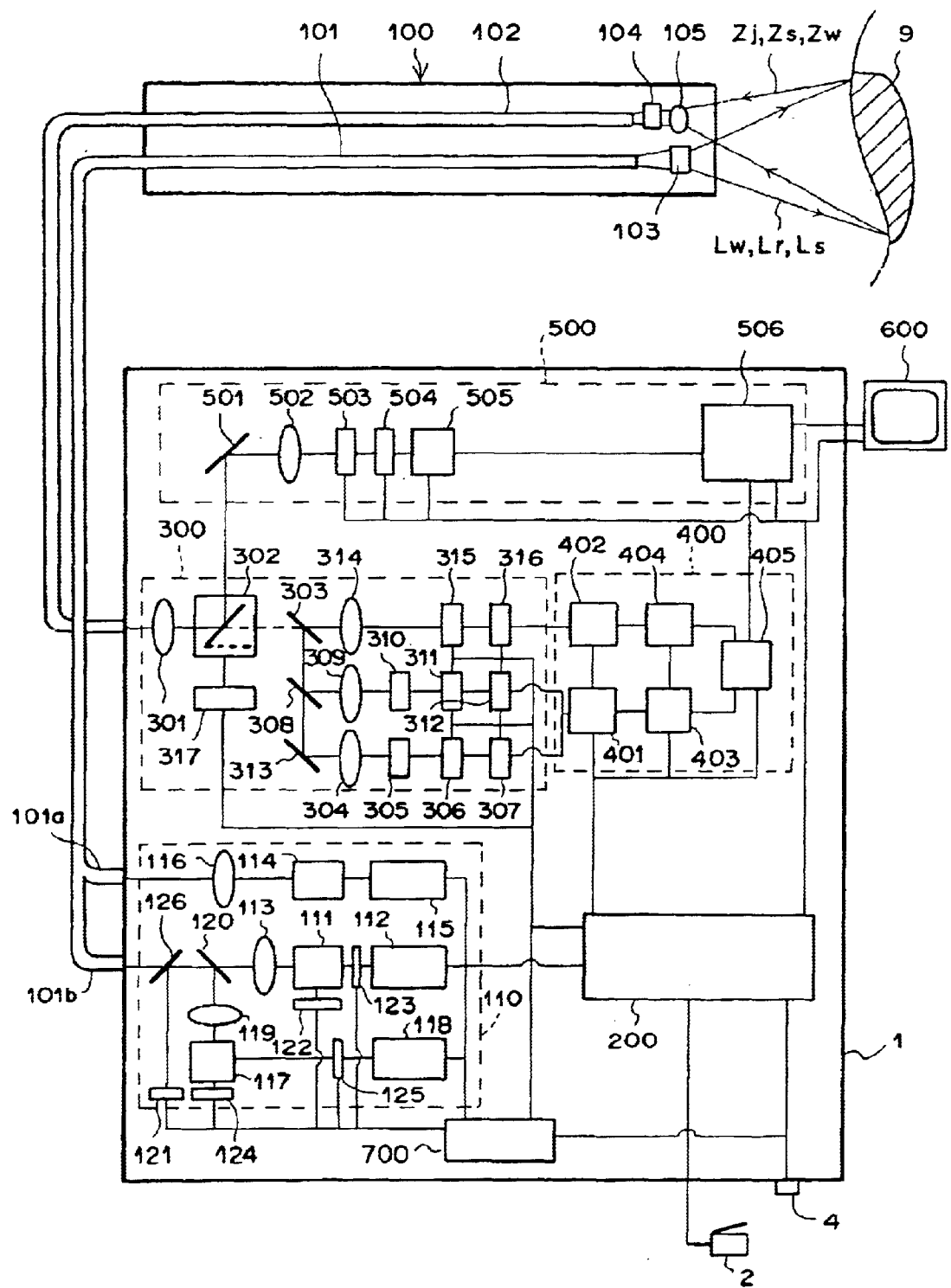
F I G . 1

FLOURESCENT— LIGHT IMAGE DISPLAY METHOD AND APPARATUS THEREFOR

BACKGROUND OF THE INVENTION

1. Field of the Invention

The present invention relates to a fluorescent-light image display method of and apparatus for measuring the fluorescent-light emitted from a target subject upon the irradiation thereof by a excitation light and displaying an image representing the data relating to the target subject.

2. Description of the Related Art

Technologies have been proposed that make use of the fact that the intensity of the fluorescent-light emitted from a normal tissue differs from the intensity of the fluorescent-light emitted from a diseased tissue when a target subject is irradiated by a excitation light having a wavelength within the wavelength range of the internal color elements of the target subject, wherein, by receiving the fluorescent-light emitted from a target subject upon the irradiation thereof by a excitation light having a wavelength within the wavelength range of the internal color elements of the target subject, the location and range of penetration of a diseased tissue is displayed as a fluorescent-light image.

Normally, when a target subject is irradiated by a excitation light, because a high-intensity fluorescent-light is emitted from a normal tissue, as shown by the solid line in FIG. 12, and a weak-intensity fluorescent-light is emitted from a diseased tissue, as shown by the broken line in FIG. 12, by measuring the intensity of the fluorescent-light emitted from aforementioned target subject, it can be determined whether the target subject is in a normal or a diseased state.

However, for cases in which the intensity of the fluorescent-light emitted from a target subject upon the irradiation thereof by a excitation light is displayed as an image, because there is unevenness on the surface of a target subject, the intensity of the excitation light irradiating the target subject is not of a uniform intensity. Further, although the intensity of the fluorescent-light emitted from the target subject is substantially proportional to the intensity of the excitation light, the intensity of aforementioned excitation light becomes weaker in inverse proportion to the square of the distance between the excitation light and the target subject. Therefore, there are cases in which the fluorescent-light received from a diseased tissue located at a position closer to the excitation light source than a normal tissue is of a higher intensity than the fluorescent-light received from a fore mentioned normal tissue, and the state of the tissue of the target subject under examination cannot be accurately discerned based solely on the data relating to the intensity of the fluorescent-light received from the target subject upon the irradiation thereof with a excitation light. In order to remedy the problems described above, the applicants of the present application propose a method of dividing two types of fluorescent-light intensities obtained of different wavelength ranges to obtain the ratio therebetween, and displaying a computed-image based on the factor obtained thereby. That is to say: propose an image display method of displaying an image based on the difference in the form of the fluorescent-light spectra reflecting the tissue-state of a target subject; a method of displaying a fluorescent-light image comprising detecting the intensity of the reflected-light reflected from a target subject upon the irradiation thereof with a reference-light composed of light in the near-infrared spectrum, which shows uniform absorption characteristics for a wide variety of target subjects, obtaining the ratio between the intensity of the reference-light and the intensity of the fluorescent-light by division, and displaying a computed-image based on the factor obtained thereby, that is, an method of obtaining a value reflecting the yield of the fluorescent-light and displaying an image; and etc.

In addition, a fluorescent-light image display apparatus according to the technology described above basically comprises a light emitting means for projecting the excitation light and illuminating-light onto a target subject, a single image obtaining means provided with separate image obtaining portions for obtaining a fluorescent-light image formed of the fluorescent light emitted from the internal color elements of the target subject and a standard-image formed of the reflected-light reflected from the target subject upon the irradiation thereof by an illuminating-light, respectively, and a display means for displaying a fluorescent-light image and a standard-image obtained by the image obtaining means. In many cases, this apparatus is incorporated into an endoscope for insertion into a body cavity of a patient, a colposcope, or a surgical-use microscope, etc. According to an apparatus of such a configuration, generally, when a measurement is to be taken, first, while viewing a displayed standard-image, an operator inserts the insertion portion into a body cavity of a patient to the vicinity of the target subject of which a measurement is to be taken. Then, the excitation light is emitted and the intensity of the fluorescent-light emitted from the target subject is measured. After a measurement has been taken, while again viewing a display of a standard-image, the operator withdraws the insertion portion from the body of the patient.

Accordingly, from the insertion of the insertion portion until the removal thereof from the body of the patient, the standard-image displaying mode must be switched to in order to safely remove the insertion portion from the body of the patient.

However, in existing methods and apparatus for fluorescent-light image display, no safety measures against any kind of irregularity in the operation of the apparatus preventing an operator from obtaining a desired image have been proposed until now. Causes that can give rise to irregularities in the operation of the apparatus that can prevent the obtaining of a desired image include, irregularities in the imaging system, reductions in the output of the light source, malfunctions occurring in the mechanical components involved in the displaying of a standard-image, and irregularities in the controlling portion that controls the mechanical elements or the control signal line.

SUMMARY OF THE INVENTION

The present invention has been developed in consideration of the circumstances described above, and it is a primary object of the present invention to provide a method and apparatus for displaying a fluorescent-light image, wherein, even for cases in which an irregularity such as one of those described above causes a state to occur in which a desired image cannot be viewed, the insertion portion can be safely and expediently removed from the body of a patient and the safety of the patient and the operator can be ensured.

The fluorescent-light image display apparatus according to the present invention comprises: a excitation light emitting means for emitting excitation light; an illuminating-light emitting means for emitting illuminating-light; a light-guiding means for guiding the excitation light and the illuminating-light to the target subject of which a measurement is to be taken; an image obtaining means provided with separate image obtaining portions for obtaining a fluorescent-light image formed of the fluorescent-light emitted from a target subject upon the irradiation thereof by a excitation light and a standard-image formed of the reflected-light reflected from the target subject upon the irradiation thereof by an illuminating-light, respectively; a display means for displaying a fluorescent-light image based on the obtained fluorescent-light image and a standard-image based on the obtained standard-image; and an image display controlling means for controlling the excitation light emitting means, the illuminating-light emitting means, the image obtaining means, and the display means; further comprising a excitation light irregularity detecting means for detecting an irregularity in the operation of the excitation light emitting means, a standard-image display controlling means for causing, in response to a detection signal from the excitation light irregularity detecting means, the illuminating-light to be emitted from the illuminating-light emitting means, the image obtaining means to be switched the standard-image obtaining mode, and the display means to be switched to the standard-image displaying mode.

Here, "image obtaining portion" refers to a imaging element, and a mirror, etc. for guiding a fluorescent-light image or a standard-image to a imaging element; further, "separate image obtaining portions" refers to the separate imaging elements used for obtaining a fluorescent-light image and a standard-image, the separate mirrors used to guide a fluorescent-light image and a standard-image to their respective separate imaging elements, or the separate positions of a mirror, that is, the separate states for obtaining a fluorescent-light image and a standard-image. Further, there can be a plurality of each of fluorescent-light image obtaining portions and standard-image obtaining portions.

In addition, an irregularity in the operation of the excitation light to be detected by the excitation light irregularity detecting means can be an irregularity in the switching ON or OFF of the power source of the excitation light source, an irregularity occurring in the electric drive-current flowing to the light source thereof, an irregularity in the cooling apparatus (air-cooling fan or a Peltier element used in cooling, etc.) of the excitation light source (if an irregularity occurs in the cooling apparatus and the excitation light source is not cooled, the emission-output of the excitation light becomes weak and it becomes impossible to obtain a fluorescent-light image), or other operational irregularity relating to the drive apparatus of the excitation light source. In short, any irregularity causing the excitation light to be emitted only at an emission-output below a prescribed value or causing the excitation light to be in a non-emitted state, thereby preventing the obtaining of a fluorescent-light image qualifies.

Further, the causing of the illuminating-light to be emitted, the switching of the image obtaining means to the standard-image obtaining mode, and the switching of the display means to the standard-image displaying mode that are to be performed when an irregularity in the excitation light is detected, are performed when the illuminating-light emitting means, the image obtaining means, and the display means, respectively, are not in the aforementioned states.

Still further, according to the fluorescent-light image display apparatus described above, for cases in which a reference-light emitting means for emitting reference-light is provided, said apparatus can also be provided with an emission-output irregularity detecting means for detecting that an irregular operation has occurred in at least one of either the excitation light emitting means or the reference-light emitting means, and a standard-image display controlling means for causing, in response to an irregularity detection signal from the emission-output irregularity detecting means, the illuminating-light to be emitted from the illuminating-light emitting means, the image obtaining means to be switched to the standard-image obtaining mode, and the display means to be switched to the standard-image displaying mode. Further, in this case, the image obtaining means is provided with a separate image obtaining portion for obtaining fluorescent-light images, standard-images, and reflected-light images formed of the reflected-light reflected from a target subject upon the irradiation thereof by the reference-light, respectively.

Here, "image obtaining portion" refers to a imaging element the same as that described above, and a mirror, etc. for guiding a fluorescent-light image, a standard-image, or a reflected-light image to a imaging element; further, "separate image obtaining portions" refers to the separate imaging elements used for obtaining a fluorescent-light image, a standard-image, and a reflected-light image, and the separate mirrors, etc. used to guide a fluorescent-light image and a standard-image to their respective separate imaging elements, or refers to the separate positions of a mirror, that is, the separate states for obtaining a fluorescent-light image, a standard-image, and a reflected-light image. Further, there can be a plurality of each of fluorescent-light image obtaining portions, standard-image obtaining portions, and reflected-light image obtaining portions.

Here, in addition to the irregularities described above occurring in the excitation light emitting means, the operational irregularities detected by the emission-output irregularity detecting means include irregularities relating to the operation of the reference-light source: irregularities in the switching ON or OFF of the power source of the reference-light source, an irregularity occurring in the electric drive-current flowing to the reference-light source, or other operational irregularity in the reference-light source drive apparatus, as well as weakening of the intensity or burning out of the reference-light source (a halogen lamp) with the passage of time. In short, any irregularity causing the reference-light to be emitted only at an emission-output below a prescribed value or causing the reference-light to be in a non-emitted state, thereby preventing the obtaining of a reflected-light image, qualifies.

Another fluorescent-light image display apparatus according to the present invention comprises: a excitation light emitting means for emitting excitation light; an illuminating-light emitting means for emitting illuminating-light; a light-guiding means for guiding the excitation light and the illuminating-light to the target subject of which a measurement is to be taken; an image obtaining means provided with separate image obtaining portions for obtaining a fluorescent-light image formed of the fluorescent-light emitted from a target subject upon the irradiation thereof by a excitation light and a standard-image formed of the reflected-light reflected from the target subject upon the irradiation thereof by an illuminating-light, respectively; a display means for displaying a fluorescent-light image based on the obtained fluorescent-light image and a standard-image based on the obtained standard-image; and an image display controlling means for controlling the excitation light emitting means, the illuminating-light emitting means, the image obtaining means, and the display means; further comprising an image-obtainment irregularity detecting means for detecting an irregularity in the operation of either of the image obtaining portions, a standard-image display controlling means for causing, in response to a detection signal of the image-obtainment irregularity detecting means, the illuminating-light to be emitted from the illuminating-light emitting means, the image obtaining means to be switched to an image obtaining portion that is not operating irregularly, and the display means to be switched to the standard-image displaying mode.

Here, for cases in which there are a plurality of respective separate image obtaining portions for obtaining each of a fluorescent-light image and a standard-image, an image obtaining portion that is not operating irregularly is switched to, in an order of predetermined priority.

In addition, if the image-obtainment irregularity detecting means is a means for detecting operational irregularities in the image obtaining portions, it can be a means for detecting any type of operational irregularity occurring in an image obtaining portion: for example, for cases in which there is a mirror that moves to a different position for each respective imaging mode of imaging a fluorescent-light image or a standard-image, it can detect a mechanical malfunction such as an irregularity in the position of the mirror; or it can detect an electrical irregularity, such as either of the separate imaging elements being in a non-functional state; and etc.

Further, the causing of the illuminating-light to be emitted, the switching of the image obtaining means to the standard-image obtaining mode, and the switching of the display means to the standard-image displaying mode that are to be performed when an irregularity in one of the image obtaining portions is detected, are performed when the illuminating-light emitting means, the image obtaining means, and the display means, respectively, are not in the aforementioned states.

Still further, according to the fluorescent-light image display apparatus described above, for cases in which a reference-light emitting means for emitting a reference-light, and a reflected-light image obtaining portion for obtaining a reflected-light image of the reflected-light reflected from a target subject upon the irradiation thereof by a reference-light emitted from the reference-light emitting means have been provided, the apparatus can be further provided with an image-obtainment irregularity detecting means for detecting that an operational irregularity has occurred in one of the image obtaining means, and a standard-image display controlling means for causing, in response to a detection signal of the image-obtainment irregularity detecting means, the illuminating-light to be emitted from the illuminating-light emitting means, the image obtaining means to be switched the standard-image obtaining mode, and the display means to be switched to the standard-image displaying mode.

Yet another fluorescent-light image display apparatus according to the present invention comprises: a excitation light emitting means for emitting excitation light; an illuminating-light emitting means for emitting illuminating-light; a light-guiding means for guiding the excitation light and the illuminating-light to the target subject of which a measurement is to be taken; an image obtaining means provided with separate image obtaining portions for obtaining a fluorescent-light image formed of the fluorescent-light emitted from a target subject upon the irradiation thereof by a excitation light and a standard-image formed of the reflected-light reflected from the target subject upon the irradiation thereof by an illuminating-light, respectively; a display means for displaying a fluorescent-light image based on the obtained fluorescent-light image and a standard-image based on the obtained standard-image; and an image display controlling means for controlling the excitation light emitting means, the illuminating-light emitting means, the image obtaining means, and the display means; and a excitation light emission control line, an illuminating-light control line, an image-obtainment control line, and a display control line electrically connected to each of the excitation light emitting means, the illuminating-light emitting means, the image obtaining means, the display means, and the image display controlling means, wherein the illuminating-light emitting means emits the illuminating-light in response to the control signal of the illuminating-light control line being in the OFF state and the image obtaining means switches to the standard-image obtaining mode in response to the control signal of the image-obtainment control line being in the OFF state; further comprising a disconnection detecting means for detecting that at least one from among the illuminating-light control line, the image-obtainment control line and the display control line has become disconnected; and a standard-image controlling means for causing the control signal of the control lines from among the illuminating-light control line, the image-obtainment control line, and the display control line that have not been disconnected to be in the OFF state.

Here, "disconnected" refers to a physical break in a control line, a bad connection between the illuminating-light means, the image obtaining means, or the display means and the image display controlling means, and etc., that is, a state in which the image display controlling means cannot send a control signal to each of aforementioned means. Further, the "OFF state" refers to the state in which there is no control signal, due to aforementioned disconnection, or there is an electrical signal the same as the state in which there is no control signal.

Further, the standard-image display controlling means can be a means that causes the control signal of a control line that has not disconnected to be in the OFF state, or that causes the control signal of all the control lines to be in the OFF state.

Still further, as per the fluorescent-light image display apparatus described above, this is the same for cases in which a reference-light emitting means for emitting a reference-light is provided.

Further still, according to the fluorescent-light image display apparatus of the present invention, for cases in which an operational irregularity occurs in the image display controlling means, an input means is provided for causing the illuminating-light emitting means to emit the illuminating-light, the image obtaining means is switched to the standard-image obtaining mode and the display means to the standard-image displaying mode, wherein the standard-image display controlling means is a means for causing, in response to an input signal from the input means, the aforementioned illuminating-light emitting means to emit the aforementioned illuminating-light, and the image obtaining means to switch to the standard-image obtaining mode and the display means to switch to the standard-image displaying mode.

Here, the input means can be provided in combination with a reset switch for causing the image display controlling means to revert to the initial state.

In addition, although the display means of the fluorescent-light image display apparatus according to the present invention is provided with a single display apparatus for switching between displaying a fluorescent-light image and a standard-image, it can also be a means provided with two separate display apparatuses for displaying a fluorescent-light image and a standard-image, respectively.

Further, regarding the image-obtainment irregularity detecting means with which the fluorescent-light image display apparatus according to the present invention is provided, for cases in which the display means is provided with two separate display apparatuses for displaying a fluorescent-light image and a standard-image, respectively, the image-obtainment irregularity detecting means causes, in response to a detection signal indicating that an operational irregularity has occurred in one of the image obtaining portions, the display apparatus, from among the two display apparatuses, that has been displaying an image obtained by the image obtaining portion for which an operational irregularity has been detected to not display the image obtained by said image obtaining portion.

Still further, in response to a detection signal indicating that an operational irregularity has occurred in one of the image obtaining portions, the image display apparatus, from among the two display apparatuses, can be a display apparatus for displaying a freeze-frame image of the image obtained by the image obtaining portion for which an operational irregularity has been detected to have occurred.

Further still, the display apparatus, from among the two display apparatuses, that has been displaying an image obtained by the image obtaining portion for which an operational irregularity has been detected can be a display apparatus for displaying, in response to a detection signal indicating that an operational irregularity has occurred in one of the image obtaining portions, a message indicating that an operational irregularity has occurred in said image obtaining portion.

Additionally, according to the fluorescent-light image display apparatus of the present invention, the excitation light is a GaN semiconductor laser beam.

According to a fluorescent-light image display apparatus of a configuration described above according to the present invention, a excitation light irregularity detecting means is provided for detecting an operational irregularity occurring in the excitation light emitting means, and in response to a detection signal therefrom indicating that an operational irregularity has occurred in the excitation light emitting means, the illuminating-light is caused to be emitted from the illuminating-light emitting means, the image obtaining means is caused to be switched the standard-image obtaining mode, and the display means is caused to be switched to the standard-image displaying mode, whereby a standard-image is displayed; therefore, the standard-image displaying mode can be automatically switched to when an operational irregularity in the excitation light emitting means is detected: For example, for cases in which the fluorescent-light image display apparatus according to the present invention is implemented in a fluorescent endoscope apparatus, the endoscope insertion portion thereof can be safely removed from the body of a patient while an operator views a standard-image.

In addition, for cases in which a reference-light emitting means for emitting reference-light is provided, an emission-output irregularity detecting means for detecting that an operational irregularity has occurred in at least one of the excitation light emitting means or the reference-light emitting means is provided, and by causing, in response to a detection signal from the emission-output irregularity detecting means, the illuminating-light to be emitted from the illuminating-light emitting means, the image obtaining means to be switched the standard-image obtaining mode, and the display means to be switched to the standard-image displaying mode, a standard-image is displayed, whereby the same effect as described above can be obtained.

Further, according to the fluorescent-light image display apparatus of the present invention, an image-obtainment irregularity detecting means for detecting that an operational irregularity has occurred in one of the image obtaining portions is provided, and by causing, in response to a detection signal from the image-obtainment irregularity detecting means, the illuminating-light to be emitted from the illuminating-light emitting means, the image obtaining means to be switched the standard-image obtaining mode, and the display means to be switched to the standard-image displaying mode, whereby a standard-image is displayed, an operational irregularity occurring in an image obtaining portion can be detected, and because the image obtaining means is automatically switched, in corresponding to said operational irregularity, to an image obtaining portion that is not operating irregularly, even for cases in which an operational irregularity occurs in the image obtaining portion involved in the displaying of a standard-image, by using an image obtaining portion that is not malfunctioning, it is possible to continuously display a standard-image.

Still further, according to the fluorescent-light image display apparatus described above, for cases in which a plurality of image obtaining portions are provided, even when an image obtaining portion malfunctions, because one of the plurality of image obtaining portions that is not malfunctioning can be switched to, continuous displaying of a standard-image can be performed with even higher reliability. For example, for a case in which three image obtaining portions are provided, a standard-image can be displayed while as many as 2 of said 3 image obtaining portions are malfunctioning.

Further still, according to the fluorescent-light image display apparatus of the present invention: the illuminating-light emitting means is a means that emits, in response to the control signal of the illuminating-light emission control line being in the OFF state, the illuminating-light; the image obtaining means is a means that switches, in response to the control signal of the image-obtaining control line being in the OFF state, to the standard-image obtaining mode; the display means is a means that switches, in response to the control signal of the display control line being in the OFF state, to the standard-image displaying mode; further comprising a disconnection detecting means for detecting that at least one control line from among the illuminating-light emission control line, the image-obtainment control line, and the display control line has been disconnected; wherein, because in response to a detection signal from the disconnection detecting means, the control signal of the control lines from among the illuminating-light emission control line, the image-obtainment control line, and the display control line that have not been disconnected are caused to be in the OFF state, and the standard-image displaying mode can be switched to, a disconnection in any of the control lines of the apparatus can be detected, and even for cases in which a control line that relays a control signal involved in the displaying of a standard-image is disconnected, a standard-image can be continuously displayed.

Additionally, when a malfunction occurs in the image display controlling means, an input means is provided for causing the illuminating-light to be emitted from the illuminating-light emitting means, the image obtaining means to switch to the standard-image obtaining mode and the display to switch to the standard-image displaying mode, wherein, because in response to an input signal from the input means, the illuminating-light emitting means is caused to emit illuminating-light, the image obtaining means is switched to the standard-image obtaining mode and the display means is switched to the standard-image displaying mode, and a standard-image can be displayed, even for cases in which the image display controlling means that outputs a control signal involved in the displaying of a standard-image malfunctions, by an input operation performed by an operator, a standard-image can be manually caused to be displayed.

Further, according to the fluorescent-light image display apparatus of the present invention, because the display means can be a single display apparatus that switches between displaying a fluorescent-light image and a standard-image, the cost of the apparatus can be reduced.

Still further, because the display means of the fluorescent-light image according to the present invention can be two separate display apparatus that displays a fluorescent-light image and a standard-image, respectively, two images can be viewed at the same time, and comparative analysis is possible.

Further still, with regard to the image-obtainment irregularity detecting means with which the fluorescent-light image display apparatus described above is provided, for cases in which the display means is provided with a 2-screen display apparatus for displaying a fluorescent-light image and a standard-image, respectively, in response to a malfunction detection signal indicating that one of the image obtaining portions has malfunctioned, because the screen, from among the two display screens, that had been displaying an image obtained by the image obtaining portion detected to have malfunctioned can be caused to not display an image or to display a freeze-frame image, a mistake in judgment on the part of an operator or confusion caused by the displaying of images due to a malfunction in an image obtaining portion can be avoided. Further, because it is possible to display a message indicating that an operational irregularity has occurred in an image obtaining portion, the operator is able to recognize that an operational irregularity has occurred in said image obtaining portion.

Even further, by using excitation light having a wavelength in the 380–420 wavelength range, which is outside of the light intensity characteristic of a normal-tissue, more reliable data of a normal-tissue can be obtained. Further, by using a GaN semiconductor laser, the size of the apparatus can be made compact and the cost reduced.

BRIEF DESCRIPTION OF THE DRAWINGS

FIG. 1 is a schematic drawing of the first embodiment of a fluorescent endoscope apparatus that is an application of a fluorescent-light image display apparatus implementing the fluorescent-light image display method according to the present invention.

DESCRIPTION OF THE PREFERRED EMBODIMENTS

Figure 2:
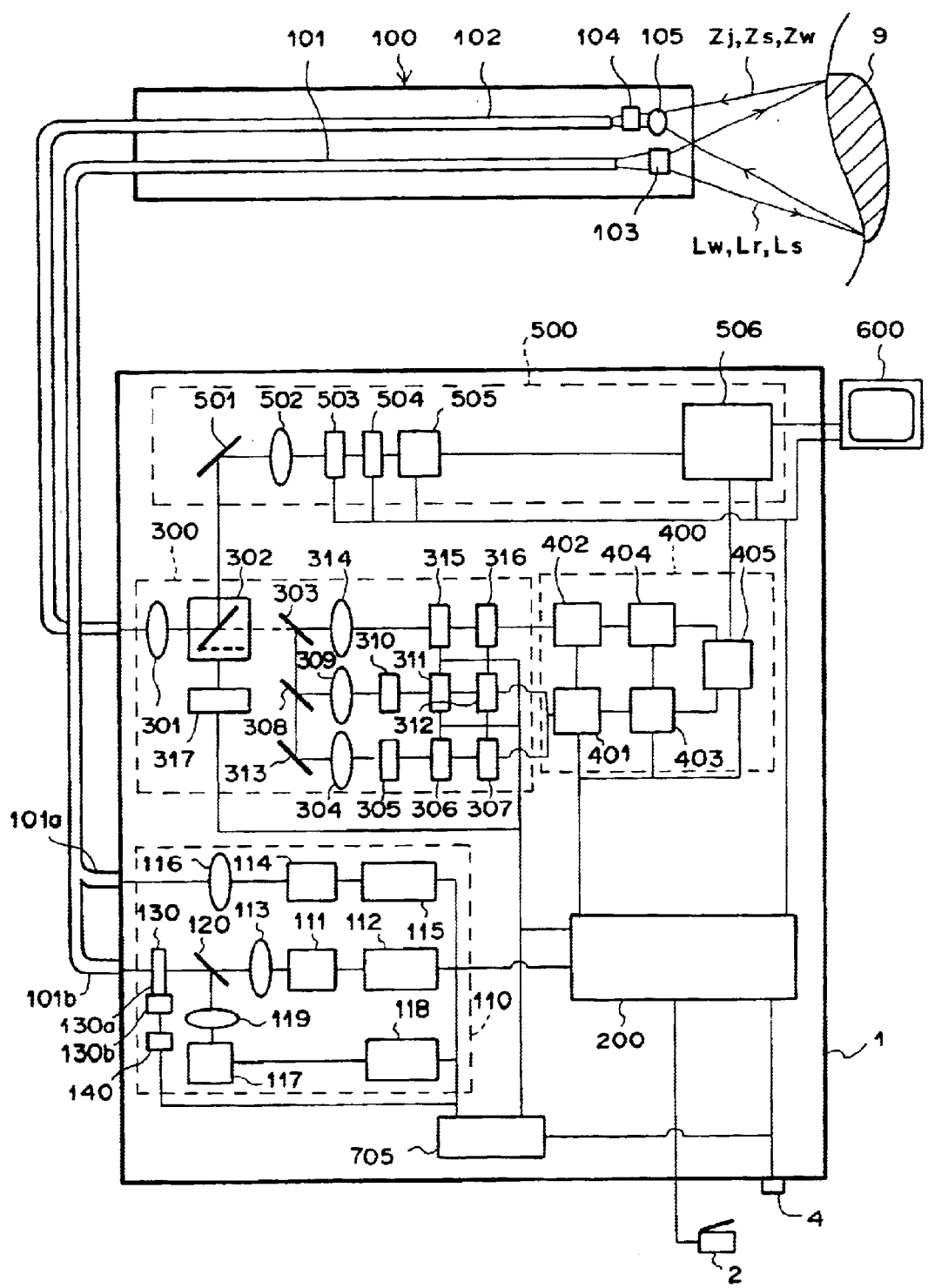
FIG. 2 is a schematic drawing of the second embodiment of a fluorescent endoscope apparatus that is an application of a fluorescent-light image display apparatus implementing the fluorescent-light image display method according to the present invention.

Hereinafter, with reference to the drawings, the preferred embodiments of the present invention will be explained.

FIG. 1 is a schematic drawing of the first embodiment of a fluorescent endoscope apparatus that is an application of a fluorescent-light image display apparatus implementing the fluorescent-light image display method according to the present invention.

The fluorescent endoscope according to the current embodiment comprises an endoscope insertion portion 100 for insertion into the body of a patient to a position near the location of the primary nidus and areas of suspected secondary infection, an image signal processing portion 1 for processing the data obtained of the target subject into an image signal, a monitor 600 for displaying as a visible-image the signal processed by the image signal processing portion 1, and a foot switch 2 for switching between a standard-image displaying mode and a composite-image displaying mode. The image signal processing portion 1 comprises: an illumination unit 110 provided with three light sources, one that emits white-light Lw for obtaining standard-images, one that emits excitation light Lr for obtaining autofluorescent-light images, and one that emits reference-light Ls for obtaining reflected-light images; an image detection unit 300 for obtaining the autofluorescent-light image Zj emitted from a target subject 9 upon the irradiation thereof by the excitation light Lr and a reflected-light image Zs formed of the reflected-light reflected from the target subject 9 upon the irradiation thereof by a reference-light Ls, and converting the obtained images to digital values and outputting 2-dimensional image data thereof; an image computing unit 400 for performing a distance correction computation, and etc. from the 2-dimensional image data of the autofluorescent-light image output from the image detection unit 300, assigning a color data to each computed value obtained thereby, assigning a brightness data to the 2-dimensional image data of the reflected-light image, and combining the two image data and outputting the composite-image formed thereby; a display signal processing unit 500 for digitizing the standard-image and obtaining a 2-dimensional image data thereof and converting said 2-dimensional data and the output signal from the image computing unit 400 to video signals and outputting said video signals, a standard-image display controlling means 700 for causing, in response to irregularities in the temperature of the GaN semiconductor laser 111 and the reference-light source 117 of the illumination unit 110, operational irregularities in the power source of the semiconductor laser drive apparatus 112 and the power source of the reference-light source drive apparatus 118, irregularities occurring in the electric drive-current and causes other than those described above that effect irregularities in the emission of the excitation light Lr and the reference-light Ls from the illumination unit 110, a switch to the standard-image displaying mode; a control computer 200 connected to each unit for controlling the operational timing thereof; a reset switch 4 for switching each unit and the monitor 600 to the standard-image displaying mode when an operational irregularity occurs in the control computer 200, and a footswitch 2 for switching between the standard-image displaying mode and the composite-image displaying mode. Note that the reset switch 4 causes the control computer to revert to the initial state.

The insertion portion 100 comprises a light guide 101 extending internally to the forward end thereof, and an image fiber 102. An illuminating lens 103 is provided at the forward end of the light guide 101; that is, at the excitation lightdistal end of the endoscope insertion portion 100. Further, the image fiber 102 is a composite glass fiber, and a excitation light cutoff filter 104 and a focusing lens 105 are provided at the forward end thereof. The light guide 101 comprises a composite glass fiber white-light guide 101a and a fused quartz fiber excitation light guide 101b bundled together in the form of an integrated cable, and the white-light guide 101a and the excitation light guide 101b are connected to the illumination unit 110. Note that the excitation light guide 101b is also a light-guide for guiding the reference-light. One end of the image fiber 102 is connected to the image detection unit 300.

The illumination unit 110 comprises: a GaN semiconductor laser 111 that emits excitation light Lr for obtaining autofluorescent-light images and a semiconductor-laser drive apparatus 112 electrically connected to said GaN semiconductor laser 111 that includes a semiconductor-laser power source; a white-light source 114 that emits white-light Lw for obtaining standard-images and a white-light source drive apparatus 115 electrically connected to said white-light source 114 that includes a white-light source power source; a reference-light source 117 that emits reference-light Ls for obtaining reference-light images and a reference-light source drive apparatus 118 electrically connected to said reference-light source 117 that includes a reference-light source power source; a dichroic mirror 120 for transmitting the excitation light Lr emitted from the GaN semiconductor laser 111 and reflecting at a right angle the reference-light Ls emitted from the reference-light source 117; a transmissive mirror 126 for substantially transmitting and reflecting at a right angle a portion of the excitation light Lr output from the GaN semiconductor laser 111 and the reference-light Ls output from the reference-light source 117; an emission-output irregularity detecting means 121 for monitoring the excitation light Lr and the reference-light Ls reflected by the transmissive mirror 126 and detecting an emission-output irregularity of the excitation light or the reference-light when the intensity of the emission-output thereof is lower than a prescribed value (including cases in which no emission is output), and outputting a detection signal indicative thereof to the standard-image display controlling means 700; a GaN semiconductor laser temperature detecting means 122 for monitoring the temperature of the GaN semiconductor laser 111 and detecting that the temperature thereof is higher than a prescribed value, and outputting a detection signal indicative of said temperature irregularity to the standard-image display controlling means 700; a reference-light source temperature detecting means 124 for monitoring the temperature of the reference-light source 117 and detecting that the temperature thereof is higher than a prescribed value, and outputting a detection signal indicative of said temperature irregularity to the standard-image display controlling means 700; a semiconductor-laser drive apparatus irregularity detecting means 123 for detecting that the semiconductor-laser power source of the semiconductor laser drive apparatus 112 does not turn ON or OFF, and that the electric drive-current of the GaN semiconductor laser is an irregular electric current, and outputting a detection signal indicative of the irregularity thereof to the standard-image display controlling means 700; and a reference-light source drive apparatus irregularity detecting means 125 for detecting that the reference-light source power source of the reference-light source drive apparatus 118 does not turn ON or OFF, and that the electric drive-current of the reference-light source is an irregular electric current, and outputting a detection signal indicative of the irregularity thereof to the standard-image display controlling means 700.

The image detection unit 300, to which the image fiber 102 is connected, comprises: a collimator lens 301 for focusing an autofluorescent-light image, a standard-image, or a reflected-light image conveyed thereto by the image fiber 102; a movable mirror 302 for totally reflecting at a right angle a standard-image passing through the collimator lens 301 and transmitting a fluorescent-light image and a reflected-light image by moving to the position indicated by the broken line; a dichroic mirror 303 for reflecting at a right angle a fluorescent-light image (formed of light having a wavelength smaller than 750 nm) passing through the collimator lens 301; a half-mirror 308 for transmitting 50% and reflecting at a right angle 50% of the quantity of light of an autofluorescent-light image reflected by the dichroic mirror 303; a fluorescent-light image mirror 313 for reflecting at a right angle the autofluorescent-light image transmitted by the half-mirror 308; a wide-band fluorescent-light image focusing lens 304 for focusing the autofluorescent-light image reflected at a right angle by the fluorescent-light image mirror 313; a wide-band band-pass filter 305 for extracting, from the autofluorescent-light image transmitted by the wide-band fluorescent-light image focusing lens 304, light having a wavelength in the 430 nm–730 nm wavelength range; a wide-band fluorescent-light image high-sensitivity imaging element 306 for obtaining the autofluorescent-light image transmitted by the wide-band band-pass filter 305; an A/D converter 307 for digitizing and outputting as a 2-dimensional image data the autofluorescent-light image obtained by the wide-band fluorescent-light image high-sensitivity imaging element 306; a narrow-band fluorescent-light image focusing lens 309 for focusing the autofluorescent-light image reflected at a right angle by the half-mirror 308; a narrow-band band-pass filter 310 for extracting, from the autofluorescent-light image transmitted by the narrow-band fluorescent-light image focusing lens 309, light having a wavelength in the 430 nm–530 nm wavelength range; a narrow-band fluorescent-light image high-sensitivity imaging element 311 for obtaining the autofluorescent-light image transmitted by the narrow-band band-pass filter 310; an A/D converter 312 for digitizing and outputting as a 2-dimensional image data the autofluorescent-light image obtained by the narrow-band fluorescent-light image high-sensitivity imaging element 311; a reflected-light image focusing lens 314 for focusing the reflected-light image transmitted by the dichroic mirror 303; a reflected-light image imaging element 315 for obtaining the reflected-light image focused by the reflected-light image focusing lens 314; an A/D converter 316 for digitizing and outputting as a 2-dimensional image data the reflected-light image obtained by the reflected-light image imaging element 315.

The image computing unit 400 comprises: an autofluorescent-light image memory 401 for storing digitized autofluorescent-light image signal data; a reflected-light image memory 402 for storing the reflected-light image signal data; an autofluorescent-light image computing portion 403 for performing computations corresponding to the ratio between each pixel value of an autofluorescent-light image formed of two different wavelength bands of fluorescent-light, stored in the autofluorescent-light image memory 401 and deriving a computed-value for each pixel, and assigning a color data to each computed value obtained thereby to form an image signal having color data; a reflected-light image computing portion 404 for assigning a brightness data to each pixel value of a reflected-light image stored in the reflected-light image memory 402; and an image composing portion 405 for combining the image signal having color data, which is output from the autofluorescent-light image computing portion 403 and the image signal having brightness data, which is output from the reflected-light image computing portion 404, and forming a composite-image.

The autofluorescent-light image memory 401 is formed of a wide-band autofluorescent-light image memory zone and a narrow-band autofluorescent-light image memory zone, which are not shown; the wide-band autofluorescent-light image obtained by the wide-band fluorescent-light image high-sensitivity imaging element 306 is stored in the wide-band autofluorescent-light image memory zone, and the narrow-band autofluorescent-light image obtained by the narrow-band fluorescent-light image high-sensitivity imaging element 311 is stored in the narrow-band autofluorescent-light image memory zone.

The display signal processing unit 500 comprises: a standard-image mirror 501 for reflecting at a right angle a standard-image reflected by the movable mirror 302; a standard-image focusing lens 502 for focusing the standard-image reflected by the standard-image mirror 501; a standard-image imaging element 503 for obtaining the standard-image focused by the standard-image focusing lens 502; an A/D converter 504 for digitizing and outputting as a 2-dimensional image data the standard-image obtained by the standard-image imaging element 503; a standard-image memory 505 for storing the digitized standard-image signal; and a video signal converting circuit 506 for converting the standard-image signal output from the standard-image memory 505 and the composite-image signal output from the image composing portion 405 to video signals and outputting said video signals. The monitor 600 is a monitor that switches between displaying a standard-image and a composite-image.

Next, the operation of the fluorescent endoscope described above that is an application of a fluorescent-light image display apparatus implementing the fluorescent-light image display method according to the present invention, will be explained.

First, the operation occurring when a composite image is to be displayed using an autofluorescent-light image formed of two different wavelength bands of fluorescent-light and a reflected-light image will be explained.

When an autofluorescent-light image formed of two different wavelength bands of fluorescent-light is to be obtained, the semiconductor drive apparatus is activated based on a signal from the control computer 200 and the excitation light Lr is emitted from the GaN semiconductor laser; the excitation light Lr is transmitted by the excitation light focusing lens 113, the dichroic mirror 120, and the transmissive mirror 126 and enters the excitation light guide 101b, and after being guided to the excitation lightdistal end of the endoscope insertion portion 100, it is projected onto the target subject 9 by the illuminating lens 103. The autofluorescent-light image emitted from the target subject 9 upon the irradiation thereof by the excitation light Lr is focused by the focusing lens 105, transmitted by the excitation light cutoff filter 104 and enters the forward end of the image fiber 102, and after passing through the image fiber 102 enters the collimator lens 301. The excitation light cutoff filter 104 is a long-pass filter that transmits all fluorescent-light having a wavelength of 420 nm and longer. Because the wavelength of the excitation light is 410 nm, the excitation light reflected from the target subject 9 is cutoff by the excitation light cutoff filter 104. The autofluorescent-light image transmitted by the collimator lens 301 is reflected at a right angle by the dichroic mirror 303, and then, is transmitted by the half-mirror 308 at a transmittance rate of 50% and reflected by the half-mirror 308 at a reflectance rate of 50%. The autofluorescent-light image transmitted by the half mirror 308 is reflected at a right angle by the fluorescent-light image mirror 313, focused by the wide-band fluorescent-light image lens 304, transmitted by the wide-band band-pass filter 305, and obtained by the wide-band fluorescent-light image high-sensitivity imaging element 306; the image signal output from the wide-band fluorescent-light image high-sensitivity imaging element 306 is input to the A/D converter 307, and after being digitized, is stored in the wide-band fluorescent-light image memory zone 401.

In addition, the autofluorescent-light image reflected by the dichroic mirror 303 and reflected by the half-mirror 308 is focused by the narrow-band fluorescent-light image focusing lens 309, transmitted by the narrow-band band-pass filter 310, obtained by the narrow-band fluorescent-light image high-sensitivity imaging element 311, input to the A/D converter 312, and after being digitized, is stored in the narrow-band fluorescent-light image memory zone 401. Note that the digital data of the autofluorescent-light image obtained by the wide-band fluorescent-light image high-sensitivity imaging element 306 and the digital data of the autofluorescent-light image obtained by the narrow-band fluorescent-light image high-sensitivity imaging element 311 are stored in respective, different zones. Note that here, the movable mirror 302 is disposed in the position parallel to the light axis of the autofluorescent-light image indicated by the broken line.

Further, the reference-light Ls emitted from the reference-light source 117 is transmitted by the reference-light focusing lens 119, reflected at a right angle by the dichroic mirror 120, transmitted by the transmissive mirror 126 and enters the excitation light guide 101b, and after being guided to the excitation lightdistal end of the endoscope insertion portion, is projected onto the target subject 9 by the illuminating lens 103. The reflected-light image formed of the reflected-light reflected from the target subject 9 upon the irradiation thereof by the reference-light Ls is focused by the focusing lens 105, and the reflected-light image transmitted by the focusing lens 105 is transmitted by the excitation light cutoff filter 104 and enters the forward end of the image fiber 102; after passing through the image fiber 102, said reflected-light image enters the collimator lens 301. The excitation light cutoff filter 104 is a long-pass filter that transmits reflected-light having a wavelength of 420 nm and longer. The reflected-light image transmitted by the collimator lens 301 is transmitted by the dichroic mirror 303, focused by the reflected-light image focusing lens 314, and obtained by the reflected-light image imaging element 315; the image signal output from the reflected-light image imaging element 315 is input to the A/D converter 316, and after being digitized, is stored in the reflected-light image memory zone 402. Note that here, the movable mirror is disposed the position parallel to the light axis of the reflected-light image indicated by the broken line.

The autofluorescent-light image formed of two different wavelength bands of fluorescent-light that has been stored in the autofluorescent-light image memory 401 is subjected to computations corresponding to the ratio between each pixel value of each image by the autofluorescent-light image computing portion 403; a color data is assigned to each computed value obtained thereby to form an image signal having color data, which is then output. Further, the reflected-light image computing portion 404 assigns a brightness value to each pixel value of the reflected-light image stored in the reflected-light image memory 402 to form an image signal having brightness data, which is then output. The image signal output from the autofluorescent-light image computing portion 403 and the image signal output from the reflected-light image computing portion 404 are combined by the image composing portion 405. The composite image composed thereof by the image composing portion 405 is DA converted by the video signal processing circuit 506, after which it is output to the monitor 600 and displayed thereon.

Next, the operation occurring when a standard-image is to be displayed will be explained. First, the white-light source drive apparatus 115 is activated based on a signal from the control computer 200 and white-light Lw is emitted from the white-light source 114. The white-light Lw emitted from the white-light source 114 enters the white-light guide 101a via the white-light focusing lens 116, and after being guided to the excitation lightdistal end of the endoscope insertion portion 100, is projected onto the target subject 9 by the illuminating lens 103. The reflected-light of the white-light Lw is focused by the focusing lens 105, transmitted by the excitation light cutoff filter 104 and enters the forward end of the image fiber 102, and after passing through the image fiber 102, enters the collimator lens 301. The excitation light cutoff filter is a long-pass filter that transmits visible light having a wavelength of 420 nm and longer. The reflected-light image transmitted by the collimator lens 301 is reflected by the movable mirror 302 and the standard-image mirror 501, and enters the standard-image focusing lens 502. The standard-image transmitted by the standard-image focusing lens is obtained by the standard-image imaging element 503. The image signal output by the standard-image imaging element 503 is input to the A/D converter 504, and after being digitized, is stored in the standard-image memory 505. The standard-image signal stored by the standard-image memory 505 is DA converted by the video signal processing circuit 506, after which it is output to the monitor 600 and displayed as a visible-image thereon.

The series of operations relating to the displaying of a composite-image and the displaying of a standard-image are controlled by the control computer 200.

Further, switching between the composite-image displaying mode and the standard-image displaying mode is performed by depressing the footswitch 2.

Here, when in the composite-image displaying mode described above, if the temperature of the GaN semiconductor laser 111 or the reference-light source become higher than a prescribed value, due to a cooling apparatus (not shown) failure (a malfunction in an air-cooling fan or Peltier element used for cooling the GaN semiconductor laser 111), etc., the temperature irregularity is detected by the GaN semiconductor laser temperature detecting means 122 or the reference-light source temperature detecting means 124, and the detection signal thereof is output to the standard-image display controlling means 700. Here, standard image controlling means 700, under control of the control computer 200, switches automatically to the standard image displaying mode due to the operation described above. Further, when the semiconductor-laser power source of the semiconductor laser drive apparatus 112 does not turn ON or OFF, and when the electric drive-current of the GaN semiconductor laser 111 is an irregular electric current (sufficient electric current doesn't flow, or excessive electric current flows), the irregularity is detected by the semiconductor-laser drive apparatus irregularity detecting means 123, and the detection signal thereof is output to the standard-image display controlling means 700. Further, when the reference-light source power source of the reference-light source drive apparatus 118 does not turn ON or OFF, and when the electric drive-current of the reference-light source is an irregular electric current, the irregularity is detected by the reference-light source drive apparatus irregularity detecting means 125, and the detection signal thereof is output to the standard-image display controlling means 700. For these cases also, in the same way, standard image controlling means 700, under control of the control computer 200, switches automatically to the standard image displaying mode due to the operation described above.

Still further, when the intensity of the excitation light or the reference-light has become lower than a prescribed value due to a cause other than one of those described above (including cases in which the excitation light or the reference-light is not being emitted), the emission-output irregularity is detected by the emission-output irregularity detecting means 121, and the detection signal thereof is output to standard-image display controlling means 700. For this case also, in the same way, standard image controlling means 700, under control of the control computer 200, switches automatically to the standard image displaying mode due to the operation described above.

Further still, for cases in which the control computer 200 malfunctions, by depressing the reset switch 4, the control computer is caused to revert to the initial state, and then, the standard-image display controlling means 700 detects that the reset switch 4 has been depressed and outputs a control signal to the control computer 200 so as to cause a standard-image to be displayed.

Additionally, according to the operations described above, when the standard-image displaying mode is switched to, the standard-image display controlling means 700, by way of the control computer 200, displays an error message on a portion of the monitor 600 (not shown) in order to inform the operator that a malfunction has occurred.

Further, for cases in which one of the malfunctions described above occurs when operating in the standard-image displaying mode, the standard-image display controlling means 700 performs only the displaying of the error message.

Still further, according to the current embodiment, although the monitor 600 is of a configuration for switching between displaying a standard-image and a composite image, two monitors can be used, and a configuration for displaying each image on one of the monitors thereof, respectively, can be adopted. In this case, when an operational irregularity such as one of those described above occurs, the monitor displaying the composite-image can be caused to not display an image, to display a freeze-frame image, or to display an error message.

Also, according to the current embodiment, a reference-light emitting means has been used, however, a reference-light emitting means can be omitted, and instead: two autofluorescent-light images of two different wavelength bands can be obtained from the autofluorescent-light image; computations performed corresponding to the ratio between each pixel value of each image and a color data assigned to each computed-value obtained thereby, and an autofluorescent-light image having color data can be displayed; or, a white-light source can be used as the reference-light source, as in the fourth embodiment described below.

In addition, aside from temperature irregularities occurring in the GaN semiconductor laser and the reference-light source occurring in the current embodiment and operational irregularities occurring in the semiconductor-laser drive apparatus and the reference-light source drive apparatus, the weakening of the intensity or breaking down of the excitation light source with the passage of time, the weakening of the intensity or burning out of the reference-light source (for cases in which the reference-light source is a halogen lamp) with the passage of time, and etc., other irregularities occurring in the excitation light source or the reference-light source can be detected, and in the same way as described above, the standard-image display mode can be switched to.

According to a fluorescent endoscope apparatus implementing a fluorescent-light image display apparatus according to the present invention of the configuration described above, when an irregularity in the temperature of the GaN semiconductor laser 111 or the reference-light source 117, an operational irregularity of the GaN semiconductor laser drive apparatus 112 or the reference-light source drive apparatus 118, or an irregularity in the emission of the excitation light or the reference-light due to a cause other than one of those described above is detected, in response to the detection signal from the detecting means that has detected an operational irregularity, that is, a detection signal from the GaN semiconductor laser temperature detecting means 122, the reference-light source temperature detecting means 124, the semiconductor laser drive apparatus irregularity detecting means 123, the reference-light source drive apparatus irregularity detecting means 125, or the emission-output detecting means 121 that have been provided therefor, the drive apparatus of the white-light source 115 is turned ON and the white-light Lw is emitted from the white-light source 114, the movable mirror 302 is switched to the position occurring in the standard-image obtaining mode, the monitor 600 is switched to the standard-image display mode, whereby a standard-image is displayed; therefore, the standard-image display mode can be automatically switched to, corresponding to the occurrence of one of the operational irregularities described above, and the endoscope insertion portion inserted into the body of a patient can be safely removed by an operator while said operator views a standard-image.

Next, with reference to the drawings, the second embodiment of the present invention will be explained.

FIG. 2 is a schematic drawing of the second embodiment of a fluorescent endoscope apparatus that is an application of a fluorescent-light image display apparatus implementing the fluorescent-light image display method according to the present invention. Note that in so far as it is not particularly required, further explanation of elements that are the same as those of the first embodiment shown in FIG. 1 has been omitted.

The fluorescent endoscope according to the current embodiment comprises: a excitation light shutter 130 for preventing the emission of the excitation light and the reference-light, which has been added to the illumination unit 110 occurring in the first embodiment; the emission-output detecting means 121 occurring in the first embodiment; a GaN semiconductor laser temperature detecting means 122; a GaN semiconductor laser drive apparatus irregularity detecting means 123; a reference-light source temperature detecting means 124; a movable-mirror position detecting means 317 for detecting operational irregularities in the movable mirror 302; and a shutter position detecting means 140 for detecting operational irregularities in the excitation light shutter, which have been added to the image detection unit 300 occurring in the first embodiment in lieu of the reference light source drive apparatus irregularity detecting means 125, and a standard-image display controlling means 705 for causing the apparatus to be switched to the standard-image display mode in response to a detection signal from the movable-mirror position detecting means 317 or the shutter position detecting means 140. The excitation light shutter 130 comprises a excitation light shutter 130a and an electromagnetic valve 130b for operating the excitation light shutter 130a.

Figure 3:
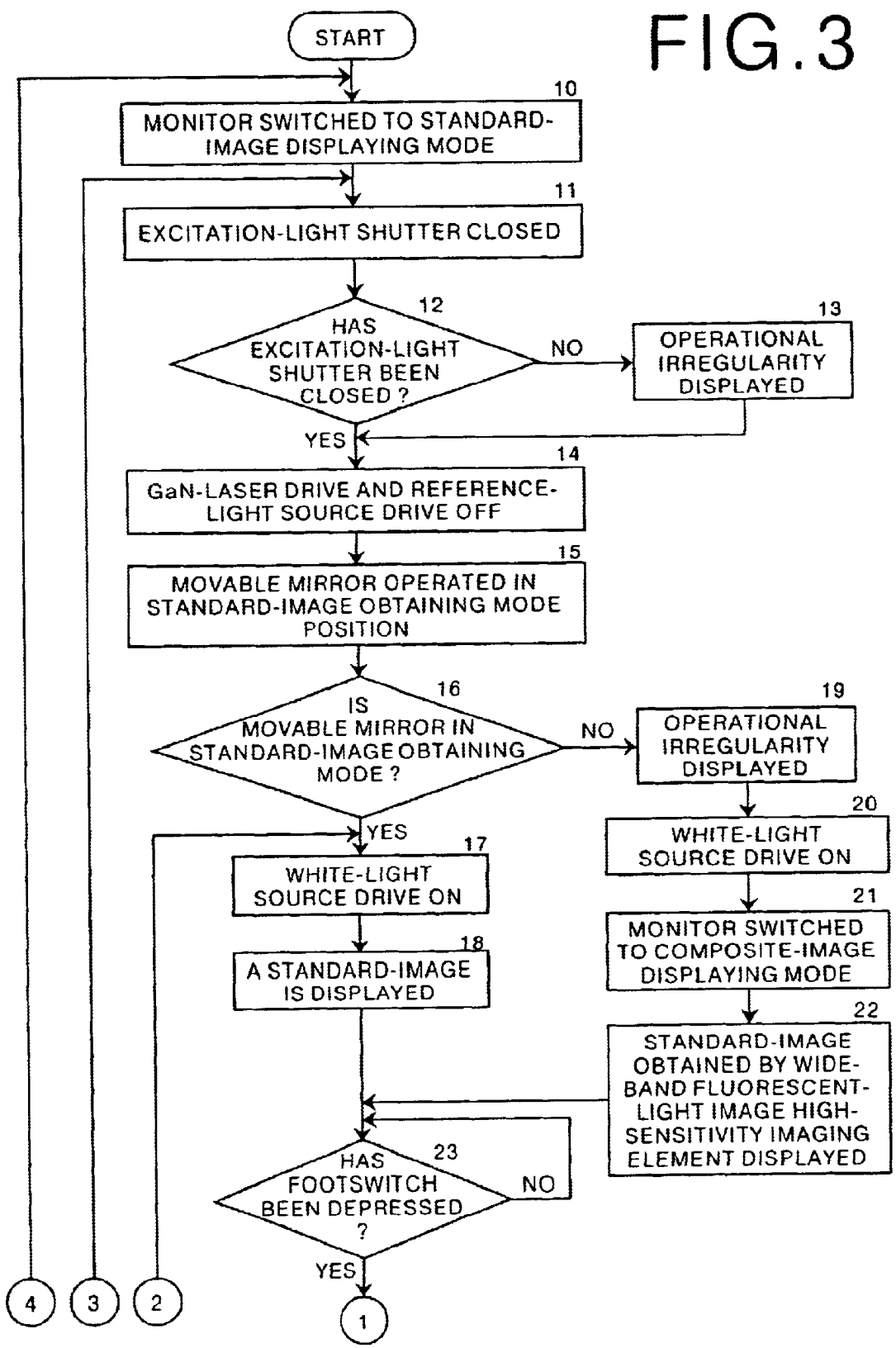
FIG. 3 is a flowchart of the operation of the second embodiment of a fluorescent endoscope apparatus shown in FIG. 1.
Figure 4:
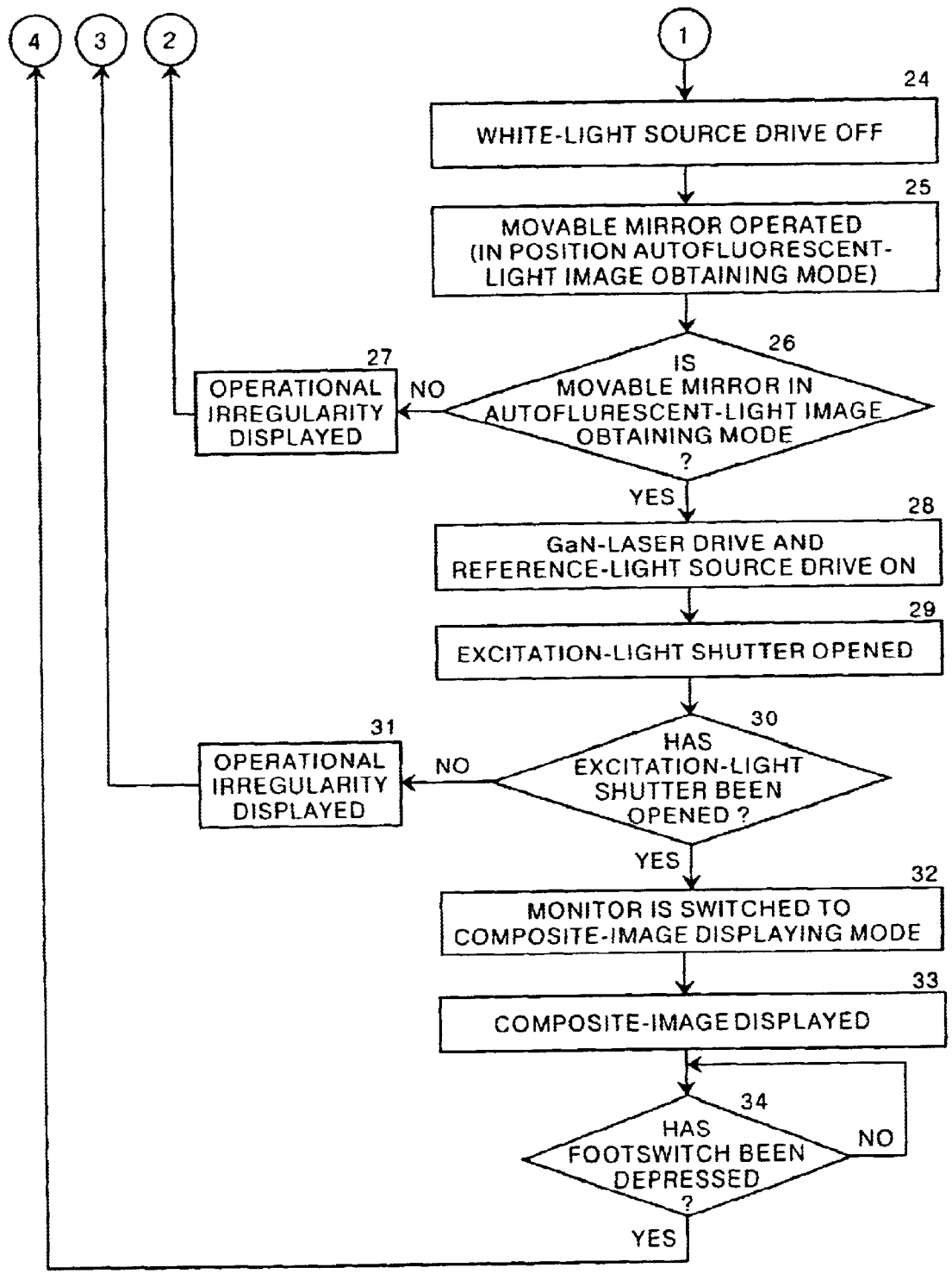
FIG. 4 is a flowchart of the operation of the second embodiment of a fluorescent endoscope apparatus shown in FIG. 2.

Next, with reference to the flow charts shown in FIGS. 3 and 4, the operation of a fluorescent endoscope implementing the fluorescent-light image display apparatus of the configuration described above according to the current embodiment will be described.

First, in step 10, the monitor 600 is switched to the standard-image displaying mode. In step 11, the excitation light shutter 130a is operated by the electromagnetic valve 130b and the excitation light shutter 130 is closed.

In step 12, a check is performed to determine whether or not the excitation light shutter 130 is closed, and for cases in which it is determined that the shutter is not closed, that the excitation light shutter 130 is not closed is detected by the shutter position detecting means 140, and step 13 is proceeded to. In step 13, the detection signal of the shutter position detecting means 140 is output to the standard-image display controlling means 705, and by way of the control computer 200, the standard-image display controlling means 705 displays a message on the monitor 600 indicating that an operational irregularity has occurred, and step 14 is proceeded to. For cases in which the excitation light shutter is determined to be closed, step 14 is proceeded to.

In step 14, for cases in which the semiconductor laser drive apparatus 112 and the reference-light source drive apparatus 118 are ON (for cases in which the standard-image display mode has been switched to from the autofluorescent-light image display mode; when the fluorescent endoscope is turned ON, they are already in the OFF state), they are turned OFF. In step 15, the movable mirror 302 is operated so as to be disposed in the position occurring in the standard-image obtaining mode so that a standard-image Zw is obtained by the standard-image imaging element 503. In step 16, a check is preformed to determine whether or not the movable mirror 302 has been disposed in the position for the standard-image obtaining mode, and for cases in which it is determined that the movable mirror has been disposed in the position for the standard-image obtaining mode, step 17 is proceeded to.

Instep 17, the white-light source drive apparatus is turned ON. In step 18, the white-light Lw is emitted from the white-light source 114, enters the white-light guide 101a through the white-light focusing lens 116, and after being guided to the excitation lightdistal end of the endoscope insertion portion 100, the white-light Lw is projected onto the target subject 9 by the illuminating lens 103. The reflected-light of the white-light Lw is focused by the focusing lens 105, transmitted by the excitation light cutoff filter 104, enters the forward end of the image fiber 102, and after passing through the image fiber 102, enters the collimator lens 301. The excitation light cutoff filter 104 is along-pass filter that transmits visible light having a wavelength of 420 nm and longer. The reflected-light image transmitted by the collimator 301 is reflected by the movable mirror 302 and the standard-image mirror 501, and enters the standard-image focusing lens 502. The standard-image transmitted by the standard-image focusing lens 502 is obtained by the standard-image imaging element 503. The image signal from the standard-image imaging element 503 is input to the A/D converter 504, and after being digitized, is stored in the standard-image memory 505. The standard-image signal stored by the standard-image memory 505 is input to the monitor 600 after being DA converted by the video signal processing circuit 506, and displayed on the monitor 600 as a visible-image.

In step 16, for cases when the movable mirror does not move to the position for obtaining a standard-image, but remains in the position for obtaining an autofluorescent-light image, that the movable mirror 302 has remained in the position for obtaining an autofluorescent-light image is detected by the movable-mirror position detecting means 317, and step 19 is proceeded to. In step 19, the detection signal of the movable-mirror position detecting means 317 is output to the standard-image display controlling means 705, and the standard-image display controlling means 705, by way of the control computer 200, displays a message on the monitor 600 indicating that an operational irregularity has occurred in the movable mirror 302, and step 20 is proceeded to. In step 20, the white-light source drive apparatus 115 is turned ON. In step 21, the monitor 600 is switched to the composite-image displaying mode. In step 22, by the same operation occurring in step 18, the reflected-light of the white-light Lw enters the collimator lens 301. Said reflected-light of the white-light Lw is transmitted by the collimator lens 301, reflected at a right angle by the dichroic mirror 303, and transmitted by the half-mirror 308 at a 50% transmittance rate; then, it is reflected at a right angle by the fluorescent-light image mirror 313, and enters the fluorescent-light image focusing lens 304. The standard-image transmitted by the fluorescent-light image focusing lens 304 is transmitted by the wide-band band-pass filter 305, and obtained by the wide-band fluorescent-light image high-sensitivity imaging element 306. The image signal from the wide-band fluorescent-light image high-sensitivity imaging element 306 is input to the A/D converter 307, and after being digitized, the standard-image is input to the monitor 600 after being DA converted by the video signal processing circuit 506, and displayed on the monitor 600 as a visible-image.

In step 23, a check is performed to determine whether or not the footswitch 2 has been depressed. For cases in which it is determined that the footswitch 2 has been depressed, step 24 is proceeded to. In step 24, the white-light drive apparatus 115 is turned OFF. In step 25, the movable mirror is operated so as to be disposed in the position for the autofluorescent-light image obtaining mode, so that the wide-band fluorescent-light image high-sensitivity imaging element 306, narrow-band fluorescent-light image high-sensitivity imaging element 311, and the reflected-light image imaging element 315 obtain an autofluorescent-light image Zj and a reflected-light image Zs. In step 26, a check is performed to determine whether or not the movable mirror is disposed in the position for the autofluorescent-light image obtaining mode, and for cases in which it has been disposed in the position for the autofluorescent-light image obtaining mode, step 28 is proceeded to. For cases in which it is determined that the movable mirror 302 has not been disposed in the position for the autofluorescent-light image obtaining mode and remains in the position for the standard-image obtaining mode, that the movable mirror 302 is not disposed in the position for the autofluorescent-image obtaining mode is detected by the movable-mirror position detecting means 317, and step 27 is proceeded to.

In step 27, the detection signal from the movable-mirror position detecting means 317 is output to the standard-image display controlling means 705, and the standard-image display controlling means 705, byway of the control computer 200, displays a message on the monitor 600 indicating that an operational irregularity has occurred in the movable mirror 302, and step 17 is returned to. In step 28, the semiconductor-laser drive apparatus 112 and the reference-light source drive apparatus 118 are turned ON. In step 29, the excitation light shutter 130a is operated by the electromagnetic valve 130b and the excitation light shutter 130 is opened. In step 30, a check is performed by the shutter position detecting means 140 to determine whether or not the excitation light shutter 130 is open, and for cases in which it is determined that the excitation light shutter 130 is not open, that the excitation light shutter 130 is not open is detected by the shutter position detecting means 140 and step 31 is proceeded to. In step 31, the detection signal from the shutter position detecting means 140 is output to the standard-image display controlling means 705, and the standard-image display controlling means 705, by way of the control computer 200, displays a message on the monitor 600 indicating that an operational irregularity has occurred in the excitation light shutter 130, and step 11 is returned to. For cases in which it has been determined that the excitation light shutter 130 is properly opened, step 32 is proceeded to.

In step 32, the monitor 600 is switched to the composite-image displaying mode. In step 33, the excitation light Lr is emitted from the GaN semiconductor laser 111, transmitted by the excitation light focusing lens 113, transmitted by the dichroic mirror 120 and enters the excitation light guide 101b, and after being guided to the excitation lightdistal end of the endoscope insertion portion 100, said excitation light Lr is projected onto the target subject 9 by the illuminating lens 103. The autofluorescent-light image emitted from the target subject 9 upon the irradiation thereof by the excitation light Lr is focused by the focusing lens 105, transmitted by the excitation light cutoff filter 104 and enters the forward end of the image fiber 102, and after passing through the image fiber 102 enters the collimator lens 301. The excitation light cutoff filter is a long-pass filter that transmits all fluorescent-light having a wavelength of 420 nm and longer. Because the excitation light Lr has a wavelength of 410 nm, the excitation light Lr reflected by the target subject 9 is cutoff by the excitation light cutoff filter 104. The autofluorescent-light image transmitted by the collimator lens 301 is reflected at a right angle by the dichroic mirror 303, and transmitted at a transmittance rate of 50% and reflected at a reflectance rate of 50% by the half-mirror 308. The autofluorescent-light image transmitted by the half-mirror 308 is reflected at a right angle by the fluorescent-light image mirror 313, and focused by the wide-band fluorescent-light image focusing lens 304. The autofluorescent-light image transmitted by the wide-band fluorescent-light image focusing lens 304 is transmitted by the wide-band band-pass filter 305, and obtained by the wide-band fluorescent-light image high-sensitivity imaging element 306; the image signal output from the wide-band fluorescent-light image high-sensitivity imaging element 306 is input to the A/D converter 307, and after being digitized, is stored in the wide-band autofluorescent-light image memory zone of the autofluorescent-light image memory 401.

Further, the autofluorescent-light image reflected by the dichroic mirror 303 and the half-mirror 308 is focused by the narrow-band fluorescent-light image focusing lens 309, transmitted by the narrow-band band-pass filter 310, and obtained by the narrow-band fluorescent-light image high-sensitivity imaging element 311; the image signal output from the narrow-band fluorescent-light image high-sensitivity imaging element 311 is input to the A/D converter 312, and after being digitized, is stored in the narrow-band autofluorescent-light image memory zone of the autofluorescent-light image memory 401. Note that the digital data of the autofluorescent-light image obtained by the wide-band fluorescent-light image high-sensitivity imaging element 306 and the digital data of the autofluorescent-light image obtained by the narrow-band fluorescent-light image high-sensitivity imaging element 311 are stored in respective, different zones. Note that here, the movable mirror 302 is disposed in the position parallel to the light axis of the autofluorescent-light image indicated by the broken line.

Still further, the reference-light Ls is emitted from the reference-light emitting means 117, and said reference-light Ls is transmitted by the reference-light focusing lens 119, reflected at a right angle by the dichroic mirror 120 and enters the excitation light guide 101b, and after being guided to the excitation lightdistal end of the endoscope insertion portion 100, said reference-light Ls is projected onto the target subject 9 by the illuminating lens 103. The reflected-light image formed of the reflected-light reflected from the target subject 9 upon irradiation thereof by the reference-light Ls is focused by the focusing lens 105. The reflected-light image transmitted by the focusing lens 105 is transmitted by the excitation light cutoff filter 104 and enters the forward end of image fiber 102, and after passing through the image fiber 102, enters the collimator lens 301. The excitation light cutoff filter is a long-pass filter that transmits reference-light having a wavelength of 420 nm and longer. The reflected-light image transmitted by the collimator lens 301 is transmitted by the dichroic mirror 303, focused by the reflected-light image focusing lens 314, and obtained by the reflected-light image imaging element 315; the image signal output from the reflected-light image imaging element 315 is input to the A/D converter 316, and after being digitized, is stored in the reflected-light image memory zone of the autofluorescent-light image memory 402. Note that here, the movable mirror 302 is disposed in the position parallel to the light axis of the reflected-light image indicated by the broken line.

The autofluorescent-light image formed of two different wavelength bands of fluorescent-light and which is stored in the autofluorescent-light image memory 401 is subjected to computations corresponding to the ratio between each pixel value of each image by the autofluorescent-light image computing portion 403, and a color data is assigned to each computed value obtained thereby to form an image signal having color data, which is then output. Further, the reflected-light image computing portion 404 assigns a brightness data to each pixel value of the reflected-light image stored in the reflected-light image memory 402 to form an image signal having brightness data, which is then output. The image signal output from the autofluorescent-light image computing portion 403 and the image signal output from the reflected-light image computing portion 404 are combined by the image composing portion 405. The composite-image composed thereof by the image composing portion 405 is input to the monitor 600 after being DA converted by the video-signal converting circuit 506, and displayed thereon. In step 34, a check is performed to determine whether or not the footswitch 2 for switching between the standard-image displaying mode and the composite-image displaying mode has been depressed. For cases in which it is determined that the footswitch 2 has been depressed, step 10 is returned to.

According to the flowchart described above, in step 12 (or, in step 30), for cases in which the shutter 30 is not closed, that is, when step 13 (or, step 31) was proceeded to, or for cases in which the movable mirror 302 was not disposed to the position for the standard-image obtaining mode in step 16, that is, when step 19 was proceeded to, or for cases in which the movable mirror 302 was not disposed in the position for the autofluorescent-light image obtaining mode in step 26, that is, when step 27 was proceeded to, up to the point at which the footswitch 2 is depressed in step 27, the series of operations occurring in each step are controlled by the control computer 200. Further, other operations are the same as those occurring in the first embodiment.

According to a fluorescent endoscope of the configuration described above implementing the fluorescent-light display apparatus according to the present invention, when an operational irregularity occurs in the excitation light shutter 130, in response to the detection signal from the shutter position detecting means 140 provided to detect said operational irregularity, the semiconductor-laser drive apparatus 112 and the reference-light drive apparatus 118 are turned OFF, which prevents the emission of the excitation light Lr and the reference-light Ls, the white-light source drive apparatus 115 is turned ON and the white-light Lw is emitted from the white-light emitting means 114, the movable mirror 302 is switched to the position for the standard-image obtaining mode, the monitor 600 is switched to the standard-image displaying mode, whereby a standard-image is displayed; therefore, the standard-image display mode can be automatically switched to, corresponding to an operational irregularity occurring in the excitation light shutter 130, and an operator can safely remove the endoscope insertion portion from the body of a patient while viewing a standard-image.

Further, a movable-mirror position detecting means 317 is provided to detect that an operational irregularity has occurred in the movable mirror 302 (when the movable mirror does not switch to the position for the standard-image obtaining mode, and remains in the position for the autofluorescent-light image obtaining mode), and in response to a detection signal therefrom, the emission of the excitation light and the reference-light is prevented, the white-light is emitted, the image obtaining mode is switched so that a standard-image is obtained by the wide-band fluorescent-light image high-sensitivity imaging element 306, the monitor 600 is switched to the standard-image displaying mode, whereby a standard-image is displayed; therefore, the standard-image display mode can be automatically switched to, corresponding to an operational irregularity occurring in the movable mirror 302.

Figure 5:
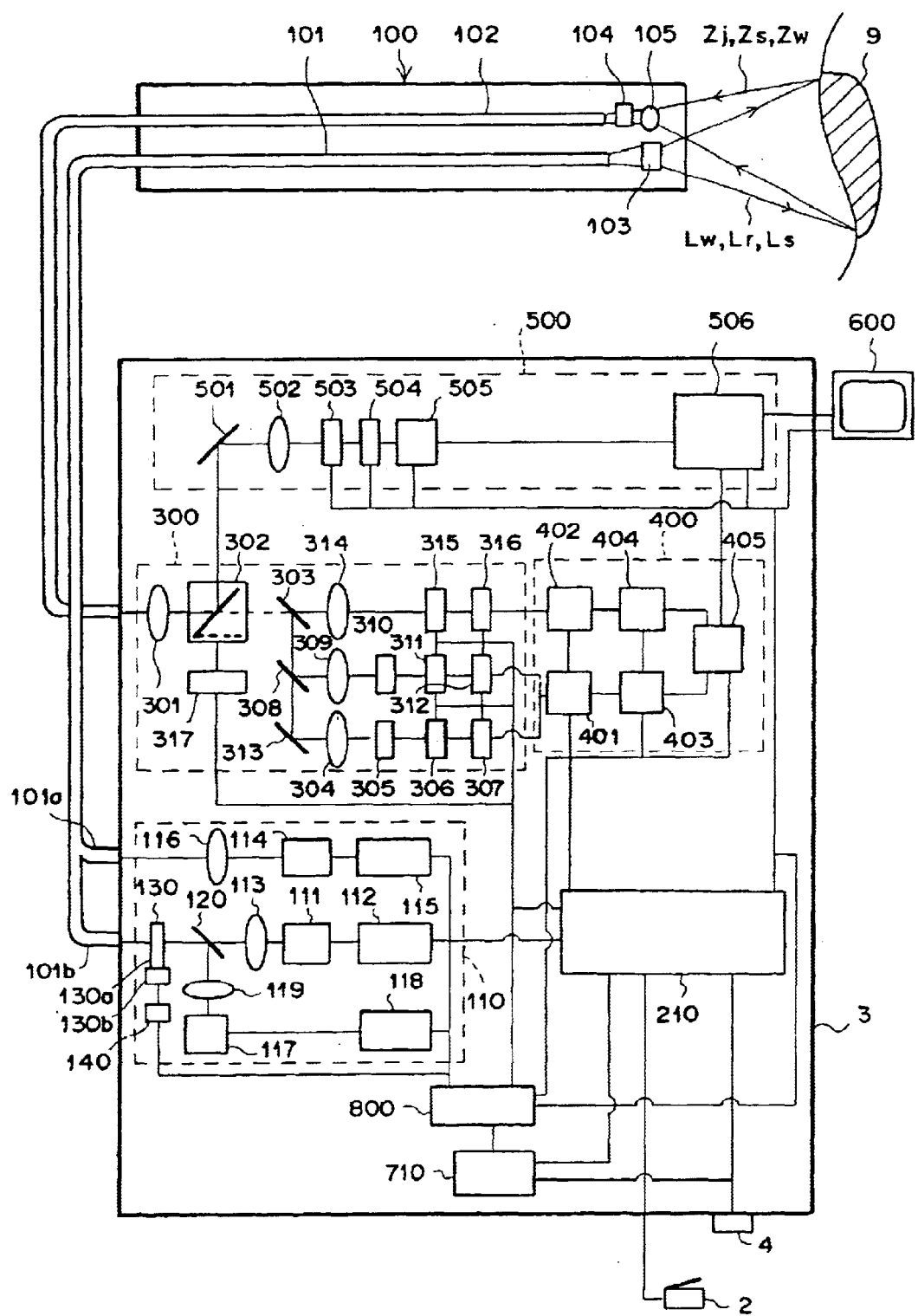
FIG. 5 is a schematic drawing of the third embodiment of a fluorescent endoscope apparatus that is an application of a fluorescent-light image display apparatus implementing the fluorescent-light image display method according to the present invention.

Next, with reference to the drawings, the third embodiment of the present invention will be explained. FIG. 5 is a schematic drawing of the third embodiment of a fluorescent endoscope apparatus that is an application of a fluorescent-light image display apparatus implementing the fluorescent-light image display method according to the present invention. Note that in so far as it is not particularly required, further explanation of elements that are the same as those of the first embodiment shown in FIG. 1 has been omitted.

The fluorescent endoscope according to the current embodiment comprises the fluorescent endoscope occurring in the first embodiment with the following modifications: the illumination unit 110 causes the white-light to be emitted when the control line connected to the control computer 200 is disconnected; the image detection unit 300 and the display signal processing means 500, in the same way as occurs in the first embodiment, switch to the standard-image obtaining mode when one of the respective control lines thereof is disconnected; further, a control-line disconnection detecting means 800 is provided for detecting that any of the controls from among the control lines connecting each unit of the image signal processing portion 3 to the monitor 600 and the control computer 210 is disconnected; and a standard-image display controlling means 710 is provided for controlling units other than a unit for which a disconnection has been detected by the control-line disconnection detecting means 800, so that the standard-image display mode is switched to.

Next, the operation of the fluorescent endoscope of the configuration described above implementing the fluorescent-light image display apparatus according to the current embodiment will be explained According to the fluorescent endoscope of the current embodiment, that any of the control lines from among the control lines connecting each unit of the image signal processing portion 3 to the monitor 600 or the control computer 210 has been disconnected is detected by the control-line disconnection detecting means 800. Then, the detection signal thereof is output to the standard-image display controlling means 710. The standard-image display controlling means 710, by way of the control computer 210, controls the units other than the unit for which a control line disconnection has been detected and the monitor 600 so that the standard-image display mode is switched to.

When any of the control lines connecting each unit and the monitor 600 to the control computer 210 becomes disconnected, the control signal thereof is detected as being an OFF signal (Here, "the control signal thereof is detected as being an OFF signal" refers to the detection of the absence of a control signal from the control computer 210 due to a disconnection.), and at this time, each unit and the monitor 600 operate so as to switch to the standard-image displaying mode. That is to say, when the control line connecting the illumination unit 110 to the control computer 210 becomes disconnected and the control signal thereof becomes an OFF signal, in response to the OFF signal, the shutter 130a is operated by the electromagnetic valve 130b and the excitation light shutter 130 is closed; further, the semiconductor-laser drive apparatus 112 and the reference-light source drive apparatus 118 are turned OFF, which prevents the emission of the excitation light Lr and the reference-light Ls,. Further, the white-light source drive apparatus 115 is turned ON, and the white-light LW is emitted from the white-light emitting means.

Further, when the control line connecting the image detection unit 300 to the control computer 210 becomes disconnected and the control signal thereof becomes an OFF signal, in response to the OFF signal, the movable mirror 302 is disposed to the position for the standard-image obtaining mode so that the standard-image imaging element 503 can obtain a standard-image.

Still further, when the control line connecting the display signal processing unit 500 to the control computer 210 becomes disconnected and the control signal thereof becomes an OFF signal, in response to the signal being in the OFF state, the standard-image reflected at a right angle by the movable mirror of the image detection unit 300 is reflected at a right angle by the standard-image mirror 501, and enters the standard-image focusing lens 502. The standard-image transmitted by the standard-image focusing lens 502 is obtained by the standard-image imaging element 503. The visible-image signal output from the standard-light image imaging element 501 is input to the A/D converter 504, and after being digitized, is stored in the standard-image memory 505. The standard-image signal stored by the standard-image memory 505 is DA converted by the video-signal processing circuit 506 and output to the monitor 600.

In addition, when the control line connecting the monitor 600 to the control computer 210 becomes disconnected and the control signal thereof becomes an OFF signal, the standard-image displaying mode is switched to, and based on an input signal from the display signal processing unit 500, a standard-image is displayed.

Additionally, when the control line connecting the image computing unit 400 to the control computer 210 becomes disconnected and the control signal thereof becomes an OFF signal, the processing to form a composite image is not performed.

When a control line connecting any one of the units and the monitor 600 to the control computer 210 becomes disconnected, the unit to which the disconnected control line is connected, in the same way as described above, switches to the standard-image displaying mode in response to an OFF control signal; the standard-image display controlling means causes an OFF signal (an electrical signal conveying the same message as if there were no control signal) to be output from the control computer 200 to the units not connected to the control line that has been disconnected, in response to a detection signal from the control-line disconnection detecting means 800, whereby the standard-image display mode is switched to and a standard-image is displayed. The other operations are the same as those occurring in the first embodiment.

According to the fluorescent endoscope of the current embodiment implementing the fluorescent-light image display apparatus according to the present invention: the white-light source drive apparatus 115 causes, in response to the control signal of the control line being in the OFF state, the white-light to be emitted; the movable mirror 302, switches, in response to the control signal of the control line being in the OFF state, to the standard-image obtaining mode; the monitor 600, switches, in response to the control signal of the control line being in the OFF state, to the standard-image obtaining mode; and a OFF signal detecting means is provided for detecting that at least one control signal of the control lines described above is in the OFF state due to a disconnection in the control line, and in response to the detection signal thereof, said OFF signal detecting means outputs an OFF signal to the control lines that have not been disconnected, and because the standard-image display mode can be switched to, a disconnection in a control line can be detected, and also, even for cases in which a disconnected control line is a control line for conveying a control signal relating to the displaying of a standard-image, a standard-image can be continuously displayed. Further, because a reset switch has been provided for causing the emission of the excitation light and of the reference-light to be prevented, the movable mirror 302 to be switched to the standard-image obtaining mode, and the monitor 600 to be switched to the standard-image display mode when an operational irregularity occurs in the control computer 210, by depressing the reset switch in response to an operational irregularity occurring in the control computer 210, an operator can force a standard-image to be displayed, and safely remove the endoscope insertion portion from the body of a patient while viewing the displayed standard-image.

Figure 6:
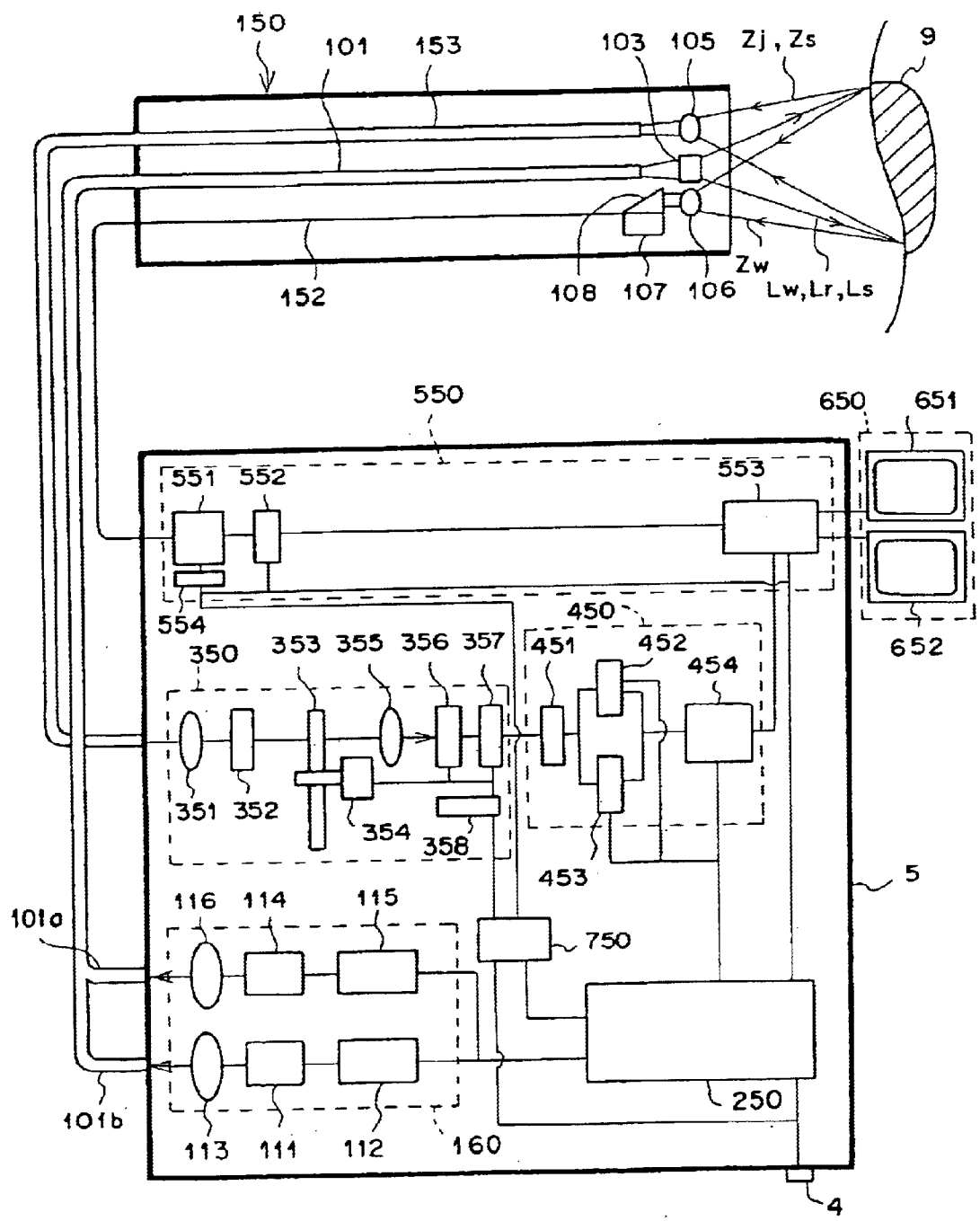
FIG. 6 is a schematic drawing of the fourth embodiment of a fluorescent endoscope apparatus that is an application of a fluorescent-light image display apparatus implementing the fluorescent-light image display method according to the present invention.

Next, with reference to the drawings, the fourth embodiment of the present invention will be explained. FIG. 6 is a schematic drawing of the fourth embodiment of a fluorescent endoscope apparatus that is an application of a fluorescent-light image display apparatus implementing the fluorescent-light image display method according to the present invention. Note that in so far as it is not particularly required, further explanation of elements that are the same as those of the first embodiment shown in FIG. 1 has been omitted.

The fluorescent endoscope according to the current embodiment comprises an endoscope insertion portion 150 for insertion into the body of a patient to a position near the location of the primary nidus and areas of suspected secondary infection, an image signal processing portion 5 for processing the data obtained of a target subject into an image signal, and a monitor 650 for displaying as a visible-image an image signal processed by the image signal processing portion 5. The image signal processing portion 5 comprises: an illuminating unit 160 provided with two light sources, one that emits white-light LW for obtaining standard-images, and one that emits excitation light Lr for obtaining autofluorescent-light images and reference-light Ls for obtaining reflected-light images; an image detection unit 350 for obtaining an autofluorescent-light image Zj formed of two different wavelength bands of fluorescent-light emitted from a target subject 9 upon the irradiation thereof by the excitation light Lr and a reflected-light image formed of the reflected-light reflected from the target subject 9 upon the irradiation thereof by the reference-light Ls, and converting the obtained images to digital values and outputting 2-dimensional image data thereof; an image computing unit 450 for performing a distance correction computation, and etc. from the 2-dimensional image data of the autofluorescent-light image output from the image detection unit 350, assigning a color data to each computed value obtained thereby, assigning a brightness data to the 2-dimensional image data of the reflected-light image output from the image detection unit 350, and combining the two image data and outputting the composite image data; a display signal processing unit 550 for digitizing the standard-image and obtaining a 2-dimensional image data thereof and converting said 2-dimensional data and the output signal from the image computing unit 450 to video signals and outputting said video signals; a standard-image display controlling means 750 connected to an AD converter output irregularity detecting means 358 of the image detecting unit 350 and an AD converter output irregularity detecting means 554 of the display signal processing unit 550, for switching, in response to a detection signal from the AD converter output irregularity detecting means 358 and the AD converter output irregularity detecting means 554 indicating that an operational irregularity has occurred in either the autofluorescent-light image high-sensitivity imaging element 356 or the standard-image imaging element 107, from the image obtaining portion for which an operational irregularity has been detected to the image obtaining portion that is not operating irregularly, and causing each unit to switch to the standard-image displaying mode; and a control computer 250 connected to each unit for controlling the operation timing thereof. Note that the AD converter output irregularity detecting means 358 and 554 occurring in the current embodiment detect an operational irregularity occurring in either the autofluorescent-light image high-sensitivity imaging element 356 or the standard-image imaging element 107 as an irregular output of the respective AD converter, and the detection signal thereof is output to the standard-image display controlling means 750.

The insertion portion 150 comprises a light guide 101 extending internally to the forward end thereof, a CCD cable 152, and an image fiber 153. An illuminating lens 103 and an objective lens 106 are provided at the forward end of the CCD cable 152 and the light guide 101, that is, at the excitation lightdistal end of the endoscope insertion portion 150. Further, the image fiber 153 is a fused quartz fiber, and a focusing lens 105 is provided at the forward end thereof. The standard-image imaging element 107 is connected to the forward end of the CCD cable 152, and a reflective prism 108 is attached to said standard-image imaging element 107. The light guide 101 comprises a composite glass fiber white-light guide 101a and a fused quartz fiber excitation light guide 101b bundled together in the form of an integrated cable, and the white-light guide 101a and the excitation light guide 101b are connected to the illumination unit 160. One end of the CCD cable 152 is connected to the display signal processing unit 550, and one end of the image fiber 153 is connected to the image detection unit 350.

The illumination unit 160 comprises: a white-light source 114 that emits white-light Lw for obtaining standard-images and a white-light source drive apparatus 115 electrically connected to said white-light source 112; a white-light focusing lens 116 for focusing the white light emitted by said white light source 114; a GaN semiconductor laser 111 that emits excitation light Lr for obtaining autofluorescent-light images and a semiconductor-laser drive apparatus 112 electrically connected to said GaN semiconductor laser 111; and a excitation light focusing lens 113 for focusing the excitation light emitted from the GaN semiconductor laser. Further, because the white-light Lw emitted by the white-light emitting means contains light of a wavelength band that can be used as a reference-light Ls, the white-light source can be used as the reference-light source.

The image detection unit 350, to which the image fiber 153 is connected, comprises: a fluorescent-light collimator lens 351 for conveying in focused form an autofluorescent-light image and a reflected-light image; a excitation light cutoff filter 352 for cutting off from the autofluorescent-light image wavelengths of light near the wavelength of the excitation light; an optical transmissive filter 353 for extracting the desired wavelengths of light from the autofluorescent-light image and the reflected-light image transmitted by the excitation light cutoff filter 352; a filter rotating means 354 for rotating the optical transmissive filter 353; a fluorescent-light focusing lens 355 for focusing the autofluorescent-light image and the reflected-light image transmitted by the optical transmissive filter 353; an autofluorescent-light image high-sensitivity imaging element 356 for obtaining the autofluorescent-light image and reflected-light image focused by the fluorescent-light focusing lens 355; an A/D converter 357 for digitizing and outputting as a 2-dimensional image data the autofluorescent-light image and the reflected-light image obtained by the autofluorescent-light image high-sensitivity imaging element 356; and an AD converter output irregularity detecting means 358 for detecting, by an irregular output of the AD converter 357, that an operational irregularity has occurred in the autofluorescent-light image high-sensitivity imaging element 356.

Figure 7:
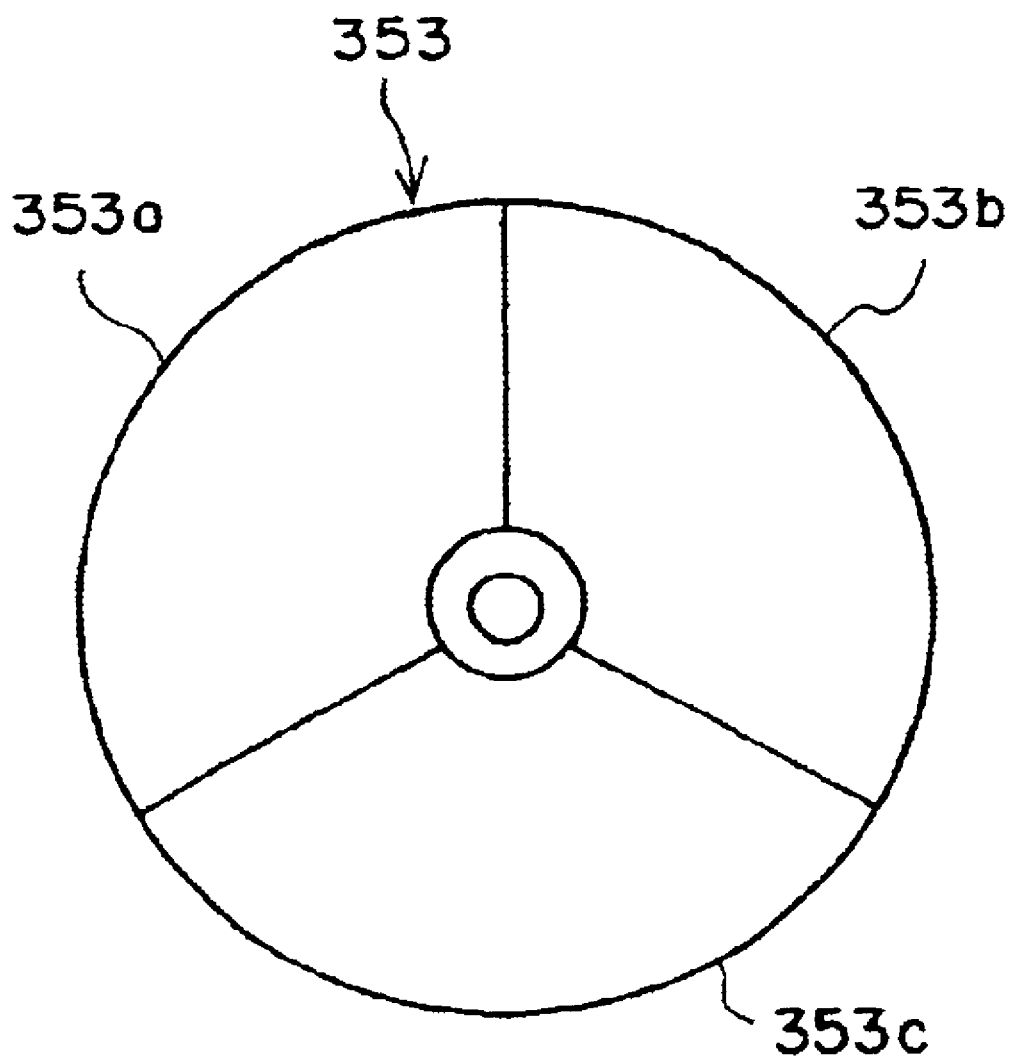
FIG. 7 is schematic drawing of the optical transmitting filter employed in the fluorescent endoscope according to the fourth embodiment.

The optical transmissive filter 353, as shown in FIG. 7, comprises three types of band-pass filters: band-pass filter 353a is a band-pass filter that transmits light having a wavelength in the 430 nm–730 nm wavelength range; band-pass filter 353b is a band-pass filter that transmits light having a wavelength in the 430 nm–530 nm wavelength range; and band-pass filter 353c is a band-pass filter that transmits light having a wavelength in the 750 nm–900 nm wavelength range.

The image computing unit 450 comprises: an image memory 451 for storing the digitized image signal data of an autofluorescent-light image and a reflected-light image; an autofluorescent-light image computing portion 452 for performing computations corresponding to the ratio between each pixel value of the autofluorescent-light image formed of two different wavelength bands of fluorescent-light and which has been stored in the image memory 451 and deriving a computed-value for each pixel, and assigning a color data to each of said computed values; a reflected-light image computing portion 453 for assigning a brightness data to each pixel value of a reflected-light image stored in the image memory 451; and an image composing portion 454 for combining the image signal having color data, which is output from the autofluorescent-light image computing portion 452 and the image signal having brightness data, which is output from the reflected-light image computing portion 453, and forming a composite-image.

The image memory 451 is formed of a narrow-band autofluorescent-light image memory zone, a wide-band autofluorescent-light image memory zone, and a reflected-light image zone, which are not shown in the figure: The autofluorescent-light image transmitted by the optical transmissive filter 353a is stored in the wide-band autofluorescent-light image memory zone; the autofluorescent-light image transmitted by the optical transmissive filter 353b is stored in the narrow-band autofluorescent-light image memory zone; and the autofluorescent-light image transmitted by the optical transmissive filter 353c is stored in the reflected-light image memory zone.

The display signal processing unit 550 comprises: an A/D converter 551 for digitizing the visible-image signal obtained by the standard-image imaging element 107; a standard-image memory 552 for storing the digitized standard-image signal; and a video signal converting circuit 553 for converting the standard-image signal output from the standard-image memory 552 and the composite-image signal output from the image composing portion 454 to video signals; and an AD converter output irregularity detecting means 554 for detecting, by an irregular output of the AD converter 551, that an operational irregularity has occurred in the standard-image imaging element 107.

The monitor unit 650 is provided with a standard-image monitor 651 and a composite-image monitor 652.

Next the operation of the fluorescent endoscope implementing the fluorescent-light image display apparatus according to the current embodiment described above will be explained.

First, the operation occurring when a composite image is to be displayed using an autofluorescent-light image formed of two different wavelength bands of fluorescent-light and a reflected-light image will be described.

When a fluorescent-light image formed of two different wavelength bands of fluorescent-light is to be obtained, the semiconductor-laser drive circuit 112 is activated based on a signal from the control computer 250, and the excitation light Lr having a wavelength of 410 nm is emitted from the GaN semiconductor laser 111. The excitation light Lr is transmitted by the excitation light focusing lens 113 and enters the excitation light guide 101b, and after being guided to the excitation lightdistal end of the endoscope insertion portion 150, said excitation light Lr is projected onto the target subject 9 by the illuminating lens 103.

The autofluorescent-light image formed of the fluorescent-light emitted from the target subject 9 upon the irradiation thereof by the excitation light Lr is focused by the focusing lens 105 and enters the forward end of the image fiber 153, and after passing through the image fiber, said autofluorescent-light image enters the excitation light cutoff filter 352. The autofluorescent-light image transmitted by the excitation light cutoff filter 352 enters the optical transmissive filter 353. Note that the excitation light cutoff filter is a long-pass filter that transmits all fluorescent-light having a wavelength of 420 nm and longer. Because the excitation light has a wavelength of 410 nm, the excitation light reflected from the target subject 9 is cutoff by the excitation light cutoff filter 352 and does not enter the optical transmissive filter 353.

The control computer activates the filter rotating apparatus 354, and after the autofluorescent-image Zj has been transmitted by the optical transmissive filter 353a, it is focused by the fluorescent-light focusing lens 355 and obtained as a wide-band autofluorescent-light image by the wide-band autofluorescent-light image high-sensitivity imaging element 356; the visible-image signal output from the wide-band autofluorescent-light image high-sensitivity imaging element 356 is input to the A/D converter 357, and after being digitized, is stored in the image data memory 451. Note that the wide-band autofluorescent-light image obtained by the wide-band autofluorescent-light image high-sensitivity imaging element 356 is stored in the wide-band autofluorescent-light image memory zone and the narrow-band autofluorescent-light image is stored in the narrow-band autofluorescent-light image memory zone of the image memory 451.

When a reflected-light image is to be obtained, the white-light source power source is activated based on a signal from the control computer 250, and the white-light Lw is emitted; this white-light Lw contains reference-light Ls having a wavelength within the 750 nm–900 nm wavelength band. The white-light Lw containing the reference-light Ls is transmitted by the white-light focusing lens 116 and enters the white-light guide 101a, and after being guided to the excitation lightdistal end of the endoscope insertion portion, it is projected onto the target subject 9 by the illuminating lens 103.

The reflected-light image formed of the reflected-light reflected from the target subject 9 upon the irradiation thereof with the white-light Lw containing the reference-light Ls is transmitted by the focusing lens 105 and enters the forward end of the image fiber 153, and after passing through the image fiber 153, said reflected-light image enters the excitation light cutoff filter 352. The reflected-light image transmitted by the excitation light cutoff filter 352 enters the optical transmissive filter 353.

The control computer activates the filter rotating apparatus 354, and after the reflected-light image has been transmitted by the band pass filter 353c, it is focused by the fluorescent-light focusing lens 355 and obtained by the wide-band autofluorescent-light image high-sensitivity imaging element 356; the image signal output from the wide-band autofluorescent-light image high-sensitivity imaging element 356 is input to the A/D converter 357, and after being digitized, is stored in the image data memory 451. Here, the band-pass filter 353c transmits the reflected-light image formed of the reflected-light reflected from the target subject 9 upon the irradiation thereof by the reference-light Ls contained in the white-light Lw. Further, the reflected-light image obtained by the wide-band autofluorescent-light image high-sensitivity imaging element 356 is stored in the reflected-light image memory zone of the image memory 451. The wide-band autofluorescent-light image and the narrow-band autofluorescent-light image stored in the image memory 451 are subjected to computations corresponding to the ratio of each pixel value of each image by the autofluorescent-light image computing portion 452, and a color data is assigned to each computed value obtained thereby to form an image signal having color data, which is then output. Further, the reflected-light image computing portion 453 assigns a brightness value to each pixel value of the reflected-light image stored in the image memory 451 to form an image signal having brightness data, which is then output. The image signal output from the autofluorescent-light image computing portion 452 and the image signal output from the reflected-light image computing portion 453 are combined by the image composing portion 454. The composite-image formed thereof by the image composing portion 454 is DA converted by the video-signal processing circuit 553, and input to the monitor 650 and displayed on the composite-image monitor 652.

Next, the operation occurring when a standard-image is to be obtained will be explained. When a normal image is to be obtained, the white-light source drive apparatus 115 is activated based on a signal from the control computer 250, and the white-light Lw is emitted from the white-light source 114. The white-light Lw enters the white-light guide 101a via the white-light focusing lens 116, and after being guided to the excitation lightdistal end of the endoscope insertion portion 150, said white-light Lw is projected onto the target subject by the illuminating lens 103. The reflected-light of the white-light Lw is focused by the objective lens 106, reflected by the reflective prism 108, and obtained by the standard-image imaging element 107. The image signal output from the standard-image imaging element 107 is input to the A/D converter 551, and after being digitized, is stored in the standard-image memory 552. The standard-image signal stored in the standard-image memory 552 is DA converted by the video-signal processing circuit 553, and input to the monitor 650 and displayed on the standard-image monitor 651 as a visible-image.

The series of operations occurring when a standard-image is to be displayed and when a composite-image is to be displayed described above are controlled by the control computer 250. Note that the obtaining of an autofluorescent-light image, a reflected-light image, and a standard-image are performed alternately in a time-division manner.

Here, when an operational irregularity occurs in either the wide-band autofluorescent-light image high-sensitivity imaging element 356 or the standard-image imaging element 107, the irregularity thereof is detected by the AD converter output irregularity detecting means 358 or the AD converter output irregularity detecting means 554, and the detection signal thereof is output to the standard-image display controlling means 750.

When an autofluorescent-light image is to be obtained: the standard-image controlling means, by way of the control computer 250, turns the semiconductor-laser drive apparatus 112 of the illumination unit 160 OFF to prevent the emission of the excitation light Lr and turns ON the white-light source 115 to cause the white-light to be emitted from the white-light source 114. For cases in which the imaging element for which an operational irregularity has been detected to have occurred is the autofluorescent-light image high-sensitivity imaging element 356, the standard-image formed of the reflected-light of the white-light is obtained by the standard-image imaging element 107 and a standard-image is displayed.

Further, for cases in which the imaging element for which an operational irregularity has been detected to have occurred is the standard image imaging element 356, the standard-image formed of the reflected-light of the white-light is obtained by the wide-band autofluorescent-light image high-sensitivity imaging element 356 and a standard-image is displayed.

Still further, when a reflected-light image or a standard-image is to be obtained, because the emission of the excitation light is already prevented and the white-light is emitted, only the switching of the imaging element, as described above, is performed, and a standard-image is displayed. Note that for cases in which the standard-image is obtained by the wide-band autofluorescent-light image high-sensitivity imaging element 356, the optical transmissive filter 353 is switched by the standard-image display controlling means 750 to the band-pass filter 353a, which transmits light having a wavelength in the 430 nm–730 nm wavelength band. Further, other operations are the same as those occurring in the first embodiment.

According to the fluorescent endoscope of the configuration described above implementing the fluorescent-light image display apparatus according to the present invention, an AD converter output irregularity detecting means 358 and an AD converter output irregularity detecting means 554 are provided for detecting that an operational irregularity has occurred in either the wide-band autofluorescent-light image high-sensitivity imaging element 356 or the standard-image imaging element 107, and in response to the detection signal thereof, the emission of the excitation light is prevented, the white-light is emitted, an imaging element that is not operating irregularly is switched to and a standard-image is displayed on the monitor 651; whereby, for cases in which an operational irregularity is detected to have occurred in an imaging element, an imaging element that is not operating irregularly can be switched to and it is possible to continuously display a standard-image.

Next, the fifth embodiment of the present invention will be explained.

Figure 8:
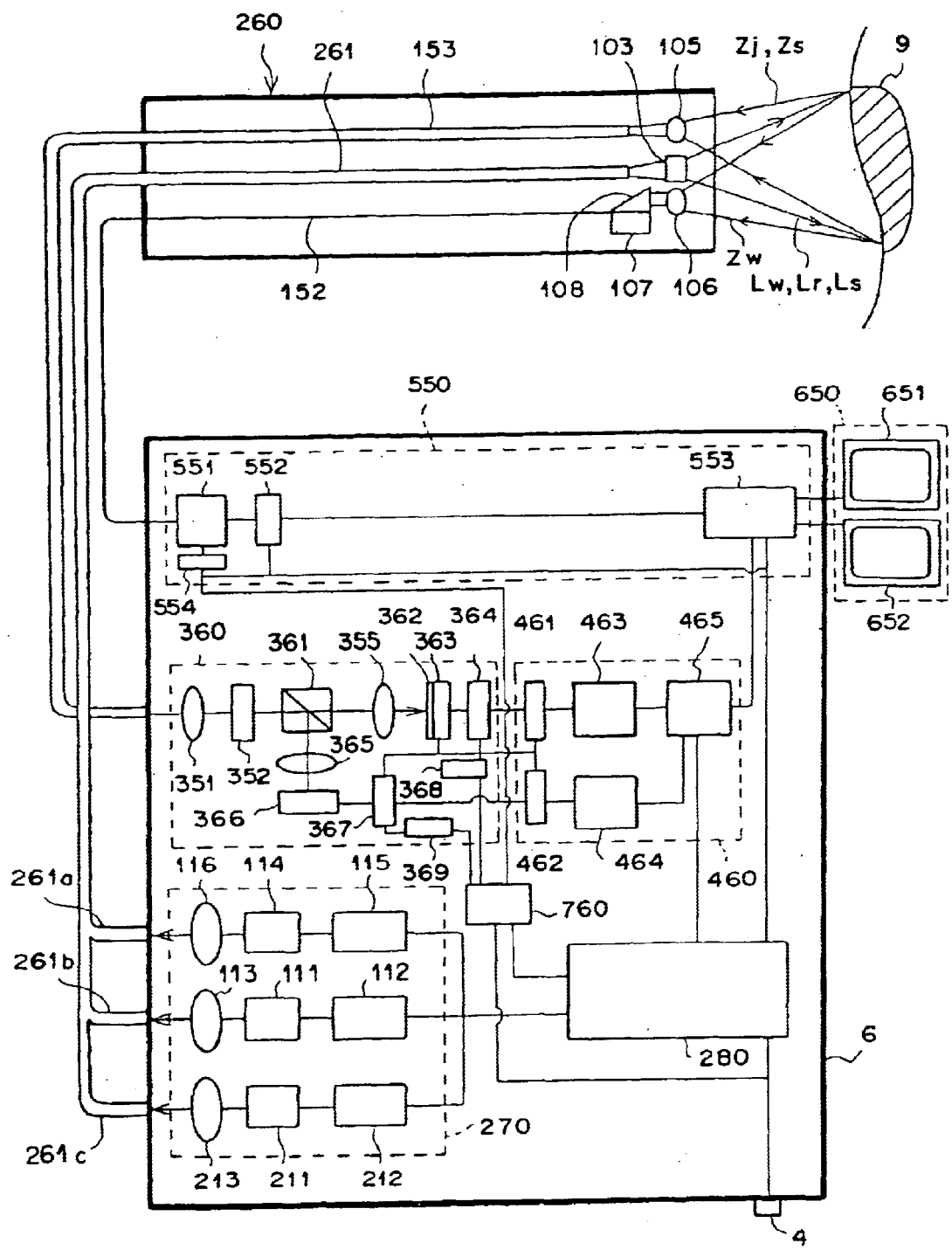
FIG. 8 is a schematic drawing of the fifth embodiment of a fluorescent endoscope apparatus that is an application of a fluorescent-light image display apparatus implementing the fluorescent-light image display method according to the present invention.

FIG. 8 is a schematic drawing of a fluorescent-light image display apparatus implementing the fluorescent-light image display method according to the present invention as implemented in a fluorescent endoscope. Note that elements that are the same as those of the fourth embodiment shown in FIG. 6 are likewise labeled, and in so far as it is not particularly required, further explanation thereof has been omitted.

The fluorescent endoscope according to the current embodiment comprises an endoscope insertion portion 260 for insertion into the body of a patient to a position near the location of the primary nidus and areas of suspected secondary infection, an image signal processing portion 6 for processing the data obtained of a target subject into an image signal, and a monitor 650 for displaying as a visible-image an image signal processed by the image signal processing portion 6. The image signal processing portion 6 comprises: an illuminating unit 270 provided with three light sources, one that emits white-light LW for obtaining standard-images, one that emits excitation light Lr for obtaining autofluorescent-light images, and one that emits reference-light Ls for obtaining reflected-light images; an image detection unit 360 for obtaining an autofluorescent-light image Zj formed of two different wavelength bands of fluorescent-light emitted from a target subject 9 upon the irradiation thereof by the excitation light Lr, and a reflected-light image formed of the reflected-light reflected from the target subject 9 upon the irradiation thereof by the reference-light Ls, and converting the obtained images to digital values and outputting 2-dimensional image data thereof; an image computing unit 460 for performing a distance correction computation, and etc. from the 2-dimensional image data of the autofluorescent-light image output from the image detection unit 350, assigning a color data to each computed value obtained thereby, assigning a brightness data to the 2-dimensional image data of the reflected-light image output from the image detection unit 360, and combining the two image data and outputting the composite image data; a display signal processing unit 550 for digitizing the standard-image and obtaining a 2-dimensional image data thereof and converting said 2-dimensional data and the output signal from the image computing unit 460 to video signals and outputting said video signals; a standard-image display controlling means 760 connected to an AD converter output irregularity detecting means 368 and an AD converter output irregularity detecting means 369 of the image detecting unit 360 and an AD converter output irregularity detecting means 554 of the display signal processing unit 550, for switching, in response to a detection signal from the AD converter output irregularity detecting means 368, 369, or 554 indicating that an operational irregularity has occurred in either the fluorescent-light image high-sensitivity imaging element 363, the reflected-light image imaging element 366 or the standard-image imaging element 107, from the image obtaining portion for which an operational irregularity has been detected to an image obtaining portion that is not operating irregularly, and the standard-image displaying mode to be switched to; and a control computer 280 connected to each unit for controlling the operational timing thereof.

The insertion portion 260 comprises a light guide 261 extending internally to the forward end thereof, a CCD cable 152, and an image fiber 153. An illuminating lens 103 and an objective lens 106 are provided at the forward end of the CCD cable 152 and the light guide 261, that is, at the excitation lightdistal end of the endoscope insertion portion 260. Further, the image fiber 153 is a fused quartz fiber, and a focusing lens 105 is provided at the forward end thereof. The standard-image imaging element 107 is connected to the forward end of the CCD cable 152, and a reflective prism 108 is attached to said standard-image imaging element 107. The light guide 261 comprises a composite glass fiber white-light guide 261a, a fused quartz fiber excitation light guide 261b, and a composite glass fiber reference-light guide 261c bundled together in the form of an integrated cable, and the white-light guide 261a, the excitation light guide 261b, and the reference-light guide 261c are connected to the illumination unit 270. One end of the CCD cable 152 is connected to the display signal processing unit 550, and one end of the image fiber 153 is connected to the image detection unit 350.

The illumination unit 270 comprises: a white-light source 114 that emits white-light Lw for obtaining standard-images and a white-light source drive apparatus 115 electrically connected to said white-light source 112; a white-light focusing lens 116; a GaN semiconductor laser 111 that emits excitation light Lr for obtaining autofluorescent-light images and a semiconductor-laser drive apparatus 112 electrically connected to said GaN semiconductor laser 111; and a excitation light focusing lens 113 for focusing the excitation light emitted from the GaN semiconductor laser; a reference-light source 211 that emits reference-light Ls for obtaining reflected-light images and a reference-light source drive apparatus 212 electrically connected to said reference-light light source 211, and a reference-light focusing lens 213 for focusing the reference-light emitted from the reference-light source 211.

The image detection unit 360, to which the image fiber 153 is connected, comprises: a fluorescent-light collimator lens 351 for conveying in focused form an autofluorescent-light image and a reflected-light image transmitted thereto by said image fiber 153; a excitation light cutoff filter 352 for cutting off from the autofluorescent-light image wavelengths of light near the wavelength of the excitation light; a dichroic mirror 361 that transmits light having a wavelength of 750 nm and higher and reflects at a right angle light having a wavelength shorter than 750 nm; a fluorescent-light image high-sensitivity imaging element 363 provided with an mosaic filter 362 mounted thereon for obtaining the fluorescent-light image transmitted by the dichroic mirror 361; an A/D converter 364 for digitizing and outputting as a 2-dimensional image data the autofluorescent-light image obtained by the fluorescent-light image high-sensitivity imaging element 363; a reflected-image imaging element 366 for obtaining the reflected-light image reflected by the dichroic mirror 361; an A/D converter 367 for digitizing and outputting as a 2-dimensional image data the autofluorescent-light image obtained by the reflected-light image imaging element 366; and AD converter output irregularity detecting means 368 and 369 for detecting, by irregular output of the AD converter 364 and 367, that an operational irregularity has occurred in the fluorescent-light image high-sensitivity imaging element 363 or the reflected-light image imaging element 366.

Figure 9:
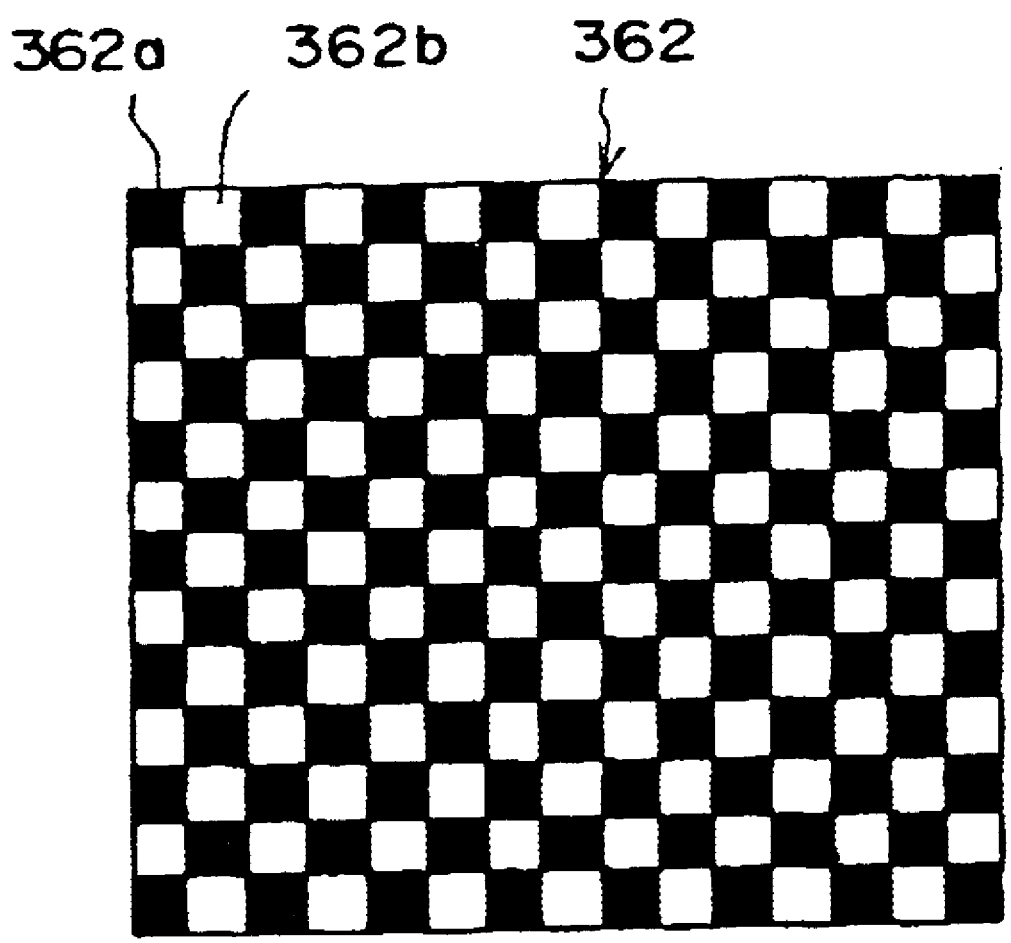
FIG. 9 is a schematic drawing of the mosaic filter employed in the fluorescent endoscope according to the fourth embodiment.

The mosaic filter 362, as shown in FIG. 9, comprises two types of microscopic optical filters: optical filter 362a is a narrow-band autofluorescent-light image optical filter that is a band-pass filter transmitting light having a wavelength in the 430 nm–530 nm wavelength range; and optical filter 362b is a wide-band autofluorescent-light image optical filter that is a band-pass filter transmitting light having a wavelength in the 430 nm–730 nm wavelength range. Each microscopic optical filter is in a 1:1 correspondence to the pixels of the fluorescent-light image high-sensitivity imaging element 363.

The image computing unit 460 comprises: an autofluorescent-light image memory 461 for storing the digitized image signal data of an autofluorescent-light image formed of two different wavelength bands of fluorescent-light; a reflected-light image memory 462 for storing the digitized image data of a reflected-light image; an autofluorescent-light image computing portion 463 for performing computations corresponding to the ratio between each pixel value of the autofluorescent-light image formed of two different wavelength bands of fluorescent-light and which has been stored in the image memory 461 and deriving a computed-value for each pixel, and assigning a color data to each of said computed values; a reflected-light image computing portion 464 for assigning a brightness data to each pixel value of a reflected-light image stored in the image memory 462; and an image composing portion 465 for combining the image signal having color data, which is output from the autofluorescent-light image computing portion 452 and the image signal having brightness data, which is output from the reflected-light image computing portion 453, and forming a composite-image.

The image memory 461 is formed of a narrow-band autofluorescent-light image memory zone, a wide-band autofluorescent-light image memory zone, which are not shown. The fluorescent-light image obtained by the pixels corresponding to the narrow-band autofluorescent-light image optical filter 362a of the fluorescent-light image high-sensitivity imaging element 363 is stored in the narrow-band autofluorescent-light image memory zone; and the fluorescent-light image obtained by the pixels corresponding to the wide-band autofluorescent-light image optical filter 362b of the fluorescent-light image high-sensitivity imaging element 363 is stored in the wide-band autofluorescent-light image memory zone.

The display signal processing unit 550 comprises: an A/D converter 551 for digitizing the image signal obtained by the standard-image imaging element 107; a standard-image memory 552 for storing the digitized standard-image signal; and a video signal converting circuit 553 for converting the standard-image signal output from the standard-image memory 552 and the composite-image signal output from the image composing portion 465 to video signals; and an AD converter output irregularity detecting means 554 for detecting, by irregular output of the AD converter 551, that an operational irregularity has occurred in the standard-image imaging element 107.

The monitor unit 650 is provided with a standard-image monitor 651 and a composite-image monitor 652.

Next the operation of the fluorescent endoscope implementing the fluorescent-light image display apparatus according to the current embodiment described above will be explained.

First, the operation occurring when a composite image is to be displayed using an autofluorescent-light image formed of two different wavelength bands of fluorescent-light and a reflected-light image will be described.

When a fluorescent-light image formed of two different wavelength bands of fluorescent-light is to be obtained, the semiconductor-laser drive circuit 112 is activated based on a signal from the control computer 280 and the excitation light Lr having a wavelength of 410 nm is emitted from the GaN semiconductor laser 111. The excitation light Lr is transmitted by the excitation light focusing lens 113 and enters the excitation light guide 261b, and after being guided to the excitation lightdistal end of the endoscope insertion portion 260, said excitation light Lr is projected onto the target subject 9 by the illuminating lens 103.

The autofluorescent-light image formed of the fluorescent-light emitted from the target subject 9 upon the irradiation thereof by the excitation light Lr is focused by the focusing lens 105 and enters the forward end of the image fiber 153, and after passing through the image fiber, said autofluorescent-light image enters the excitation light cutoff filter 352. The autofluorescent-light image transmitted by the excitation light cutoff filter 352 enters the dichroic mirror 361. Note that the excitation light cutoff filter is a long-pass filter that transmits all fluorescent-light having a wavelength of 420 nm and longer. Because the excitation light has a wavelength of 410 nm, the excitation light reflected from the target subject 9 is cutoff by the excitation light cutoff filter 352 and does not enter the dichroic mirror 361.

The autofluorescent-light image Zj transmitted by the excitation light cutoff filter 352 is focused by the fluorescent-light focusing lens 355 and enters the mosaic filter 362 mounted on the fluorescent-light image high-sensitivity imaging element 363.

The fluorescent-light transmitted by the narrow-band autofluorescent-light image optical filter 362a of the mosaic filter becomes a narrow-band autofluorescent-light image, and the fluorescent-light transmitted by the wide-band autofluorescent-light image optical filter 362a of the mosaic filter becomes a wide-band autofluorescent-light image.

The narrow-band autofluorescent-light image and the wide-band autofluorescent-light image fluorescent-light image are obtained by the high-sensitivity imaging element 363; the visible-image signal output by the fluorescent-light image high-sensitivity imaging element 363 is input to the AD converter 357, and after being digitized, are stored in the autofluorescent-light image memory 461.

The narrow-band autofluorescent-light image and the wide-band autofluorescent-light image fluorescent-light image stored in the autofluorescent-light image memory 461 are subjected to computations by the autofluorescent-light image computing portion 463 for corresponding to the ratio between each pixel value of each image to derive computed-value for each pixel, and a color data is assigned to each computed-value obtained thereby to form an image signal having color data, which is then output.

When a reflected-light image is to be obtained, the reference-light drive apparatus 212 is activated based on a signal from the control computer 280 and the reference-light Ls is emitted. The reference-light Ls is transmitted by the reference-light focusing lens 213 and enters the reference-light guide 261c, and after being guided to the excitation lightdistal end of the endoscope insertion portion 260, said reference-light Ls is projected onto the target subject 9 by the illuminating lens 103.

The reflected-light image formed of the reflected-light reflected-from the target subject 9 upon the irradiation thereof with the reference-light Ls is focused by the focusing lens 105 and enters the forward end of the image fiber 153, and after passing through the image fiber 153, said reflected-light image enters the excitation light cutoff filter 352. The reflected-light image transmitted by the excitation light cutoff filter 352 enters the dichroic mirror 361. Because the dichroic mirror 361 reflects at a right angle light having a wavelength of 750 nm and longer, the reflected-light of the reference-light is reflected, focused by the reflected-light image focusing lens 365, and obtained by the reflected-light image imaging element 366. The image signal output from the reflected-light image imaging element 366 is input to the A/D converter 367, and after being digitized, is stored as a two-dimensional image data by the reflected-light image memory 462. The reflected-light image computing portion 464 assigns a brightness data to each pixel value of the reflected-light image stored by the reflected-light image memory 462 to form an image signal having brightness data, which is then output. The image signal output from the fluorescent-light image computing portion 464 and the image signal output from the reflected-light image computing portion are combined by the image composing portion 465 to form a composite-image. The composite-image signal formed by the image composing portion 465 is DA converted by the video-signal processing circuit 553 and input to the monitor 650, and displayed on the composite-image monitor 652.

Next, the operation occurring when a standard-image is to be obtained will be explained. When a standard-image is to be displayed, the white-light source drive apparatus 115 is activated based on a signal from the control computer 280 and white-light Lw is emitted from the white-light source 114. The white-light Lw emitted from the white-light source 114 enters the white-light guide 261a via the white-light focusing lens 116, and after being guided to the excitation lightdistal end of the endoscope insertion portion 260, said white-light Lw is projected onto the target subject 9 by the illuminating lens 103. The reflected-light of the white-light Lw is focused by the objective lens 106, reflected by the reflective prism 108, and obtained by the standard-image imaging element 107. The image signal output by the standard-image imaging element 107 is input to the A/D converter 551, and after being digitized, is stored in the standard-image memory 552. The standard-image signal stored by the standard-image memory 552 is DA converted by the video signal processing circuit 553, after which it is output to the monitor 650 and displayed on the standard-image monitor 651 as a visible-image.

The series of operations described above occurring when a composite-image is to be displayed and when a standard-image is to be displayed are controlled by the control computer 280.

Figure 10:
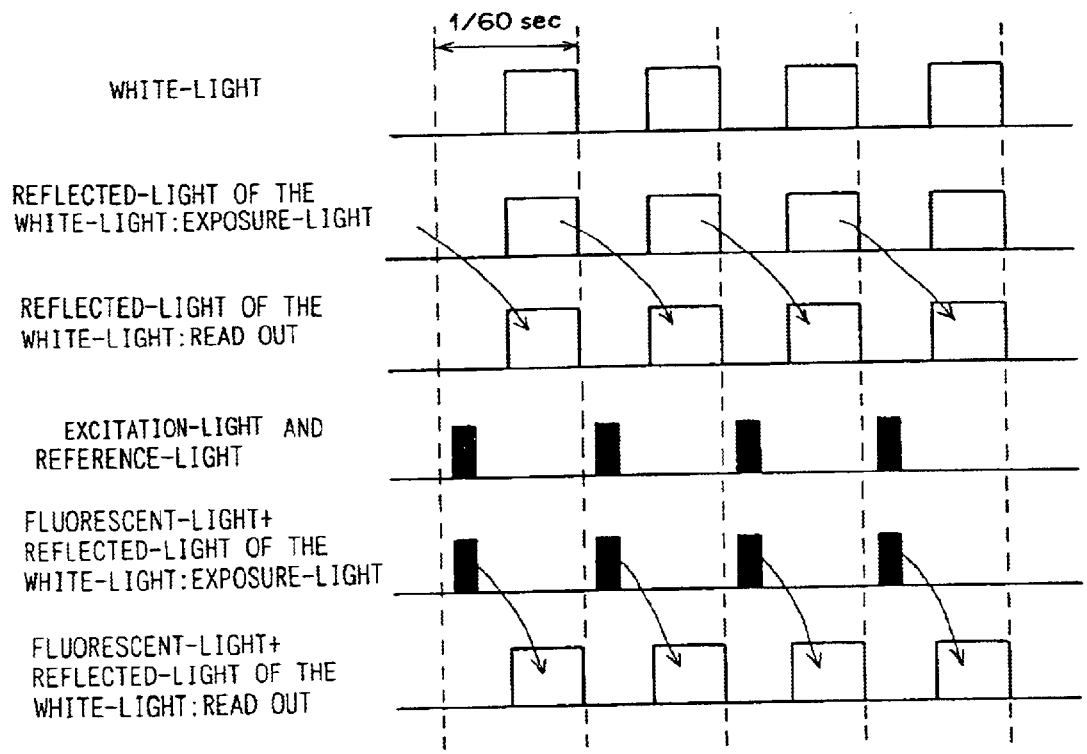
FIG. 10 is a timing chart showing the readout timing of the exposure and autofluorescent-light of the excitation light and the reference light, and the reflected-light of the white-light and the reflected-light of the reference-light occurring in the fluorescent endoscope according to the fifth embodiment.

Note that, as shown in the timing chart depicted in FIG. 10, in carrying out the exposing and reading out of each of the imaging elements' output by the emitting of the white-light, and the excitation light and the reference-light, the excitation light and the reference-light, and the white-light are controlled so as to be emitted at respectively different timings: at an emission timing of a one frame interval every 1/60 sec, so as to mutually not interfere, and because the excitation light and the reference-light are of mutually different wavelengths, the taking of a measurement is not hindered due to the emission of the respective other light.

Here, for cases in which an operational irregularity has occurred in the fluorescent-light image high-sensitivity imaging element 363, the standard-image imaging element 107, or the reflected-light image imaging element 366, the irregularity thereof is detected by the AD converter output irregularity detecting means 368, 369, or 554, and the detection signal thereof is output to the standard-image display controlling means 760.

Here, the for cases in which an autofluorescent-light image or a reflected-light image is to be obtained, the standard-image display controlling means 760, byway of the control computer 280, turns OFF the semiconductor-laser drive apparatus 112 and the reference-light source drive apparatus 118 of the illuminating unit 270, thus preventing the emission of the excitation light Lr and the reference-light Ls, and turns ON the white-light source drive apparatus 115, causing the white-light Lw to be emitted from the white-light source 114.

For cases in which an imaging element that has been detected to be operating irregularly is the fluorescent-light image high-sensitivity imaging element 363, the standard-image formed of the reflected-light of the white-light is obtained by the standard-image imaging element 107, and the standard-image displayed.

For cases in which the standard-image imaging element 107 is also operating irregularly, the standard-image formed of the reflected-light of the white-light is obtained by the reflected-light image imaging element 366, and the standard-image displayed.

Further, for cases in which an imaging-element that has been detected to be operating irregularly is the standard-image imaging element 107, the standard-image formed of the reflected-light of the white-light is obtained by the fluorescent-light image imaging element 363, and the standard-image displayed; for cases in which the fluorescent-light image imaging element 363 is also operating irregularly, the standard-image formed of the reflected-light of the white-light is obtained by the reflected-light image imaging element 366, and the standard-image displayed.

Still further, for cases in which an imaging-element that has been detected to be operating irregularly is the reflected-light image imaging element 366, the standard-image formed of the reflected-light of the white-light is obtained by the standard-image imaging element 107, and the standard-image displayed; for cases in which the standard image imaging element 107 is also operating irregularly, the standard-image formed of the reflected-light of the white-light is obtained by the fluorescent-light image imaging element 363, and the standard-image displayed.

According to the fluorescent endoscope of the configuration described above implementing the fluorescent-light image display apparatus according to the present invention, AD converter output irregularity detecting means 368, 369, and 554 are provided for detecting that an operational irregularity has occurred in any of imaging elements from among the fluorescent-light image high-sensitivity imaging element 363, the standard-image imaging element 107, and the reflected-light image imaging element 366, and in response to the detection signal thereof, the emission of the excitation light and of the reference-light is prevented, the white-light is emitted, an imaging element that is not operating irregularly is switched to and a standard-image is displayed on the monitor 651; whereby; for cases in which an operational irregularity is detected to have occurred in an imaging element, an imaging element that is not operating irregularly can be switched to and it is possible to continuously display a standard-image. Moreover, because the apparatus is equipped with three imaging elements, the standard-image can be continuously displayed with a higher degree of reliability with as many as two of the three imaging elements operating irregularly.

Figure 11:
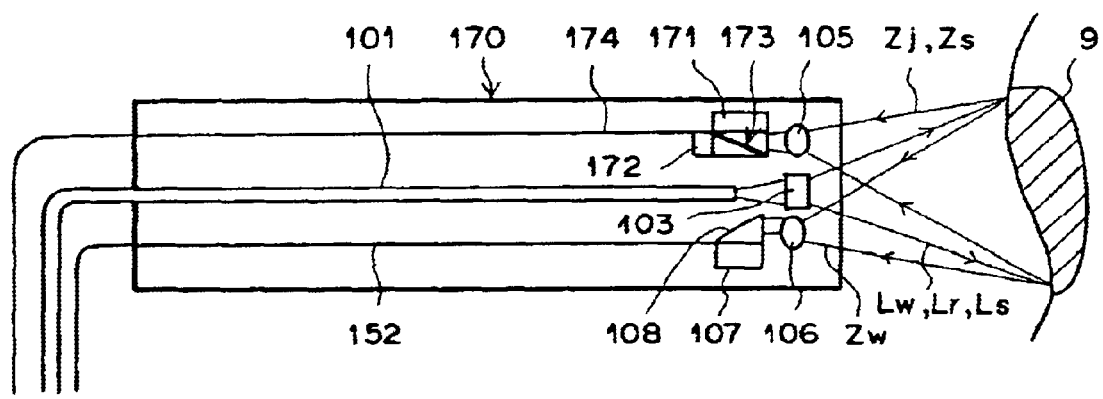
FIG. 11 is a schematic drawing of the high-sensitivity fluorescent-light imaging element and the reflected-light imaging element occurring in the fluorescent endoscopes according to the fourth and fifth embodiments for a cases in which said imaging elements are disposed in the excitation lightdistal end of the endoscope insertion portion.
Figure 12:
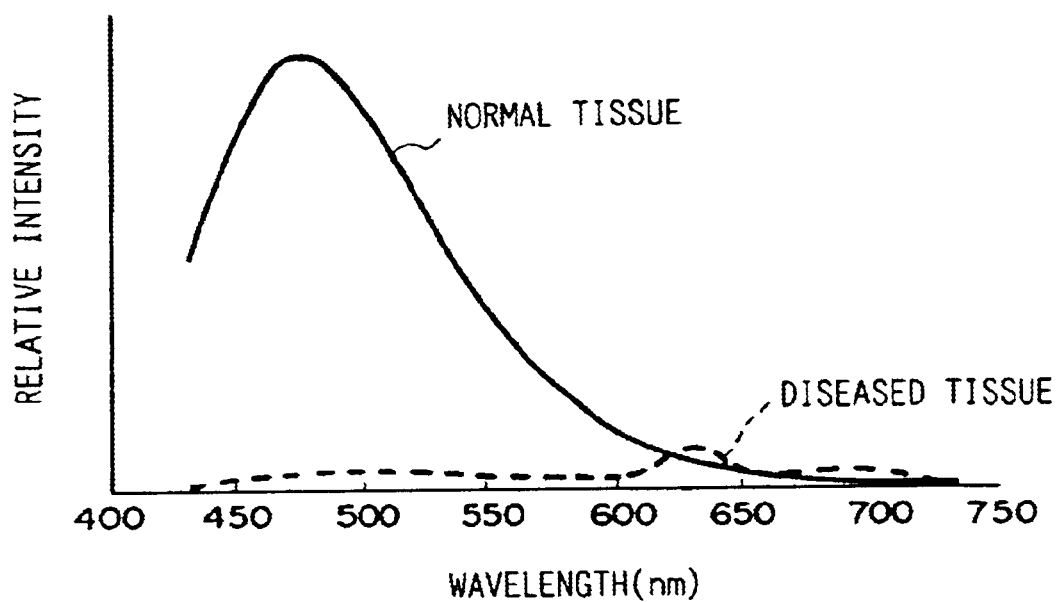
FIG. 12 is a graph provided for explanation of the intensity distribution of the fluorescent-light spectra of a normal-tissue and a diseased tissue.

According to the fourth and fifth embodiments described above, the fluorescent-light image imaging element and the reflected-light image imaging element are not housed within the image signal processing portion, and can be disposed at the excitation lightdistal end of the endoscope insertion portion. A drawing of such a configuration is shown in FIG. 11. The endoscope insertion portion 170 is provided with a fluorescent-light CCD cable 174 extending internally to the forward end thereof. The fluorescent-light image high-sensitivity imaging element 171 and the reflected-light image imaging element 172 are connected to the forward end of the fluorescent-light CCD cable 174; and a reflecting prism 173 which transmits a reflected image of a reference light and reflects at a right angle fluorescent light of the excitation light is mounted there between target excitation light. The fluorescent-light image focused by the focusing lens 105 is reflected by the reflective prism 173, and obtained by the fluorescent-light image high-sensitivity imaging element 171. The reflected-light image formed of the reflected-light reflected from the target subject 9 upon the irradiation thereof by the reference-light LS is transmitted by the reflective prism 173, and obtained by the reflected-light image imaging element 172. The obtained autofluorescent-light image and reflected-light image are output to the image processing portion through the fluorescent-light CCD cable 174. Note that when a fluorescent endoscope of such a configuration is implemented in the fourth embodiment, the fluorescent-light image high-sensitivity imaging element 171 must be provided with the mosaic filter 362 mounted thereon occurring in the fifth embodiment.

Further, the monitor from among the standard-image monitor 651 and the composite-image monitor 652 that has been displaying the image obtained by an imaging element that has been detected to be operating irregularly can be caused to not display an image, to display a freeze-frame image, or to display an error message indicating that an operational irregularity of an imaging element has occurred.

Still further, regarding the method of displaying a composite image, although the standard-image monitor 651 and the composite-image monitor 652 are provided for displaying separate images, a single monitor combining the functions for displaying both images can be used. In this case, the method of switching between the displaying of a standard-image and a composite-image can be performed automatically in a time series manner controlled by the control computer, or can be a method whereby the displaying of the images is switched at will by an operator through an appropriate switching means. Further, the standard-image and the composite-image can be superposed and displayed.

Additionally, the image fiber 153 can be formed of a composite glass fiber instead of a fused quartz fiber. Here, because fluorescent-light is emitted from the composite fiber upon the irradiation thereof to the excitation light, a excitation light cutoff filter 352 must be disposed between the focusing lens 105 and the autofluorescent-light image input face of the image fiber 153. By switching from a fused quartz fiber to a composite glass fiber, the cost of the apparatus can be reduced.

Further still, although an operational irregularity occurring in an imaging element has been detected by an output irregularity of the respective AD converter, it is also possible to detect an operational irregularity occurring in an imaging element as an irregular electric drive-current occurring in the imaging element drive circuit (not shown). Further, a configuration wherein both an operational irregularity occurring in the output of an AD converter and an irregularity in the drive-current of an imaging element drive circuit are detected can be adopted.

In addition, according to each of the embodiments described above, the computational processing performed by the autofluorescent-light image computing portion, the reflected-light image computing portion, and the image composing portion is not limited to being performed for each pixel position: the computational processing can be performed for pixel units corresponding to binning processing carried out by the fluorescent-light image high-sensitivity imaging element; or a horizontal×vertical block (n×m) of pixels desired by an operator. Alternatively, computational processing can be performed only on a pixel area specified by an operator, or, a selection of pixel areas determined based on consideration of the volume of computation required for processing.

Further, for cases in which there are pixel regions for which computational processing has not been performed, by displaying said regions in a predetermined color, the regions for which computational processing has been performed can be clearly displayed. For cases in which the pixel regions to be subjected to computational processing have been spaced apart, etc., compensated displaying can be performed based on the results of the computational processing performed for adjacent regions.

Still further, as to the excitation light source, any excitation light source producing excitation light having a wavelength in the 400 nm–420 nm wavelength range can be adopted.

Even further still, although the excitation light source and the white-light source have been provided as separate light sources, by use of an appropriate optical filter, the light source can be made into a combined light source.

Also, the fluorescent-light image display apparatus according to the present invention can also be implemented in an apparatus for detecting the fluorescent-light emitted from a target subject, which has absorbed a fluorescent diagnostic chemical, upon the irradiation thereof by a excitation light.

What is claimed is:

1. A method of displaying a fluorescent-light image comprising
    irradiating a target area with an illuminating light and a excitation light emitted from a excitation light emitting means and a reference-light emitted from a reference-light emitting means and which have been guided to said target area,
    obtaining, by use of a single image obtaining means provided with separate image obtaining portions for obtaining a fluorescent-light image, a standard-image, and a reflected-light image, respectively, a fluorescent-light image formed of the fluorescent-light emitted from the target area upon the irradiation thereof by the excitation light, a standard-image formed of the reflected-light reflected from the target area upon the irradiation thereof by the illuminating light, and a reflected-light image formed of the reflected-light reflected from the target area upon the irradiation thereof by the reference-light, and
    displaying a fluorescent-light image based on the obtained fluorescent-light image and the obtained reflected-light image and a standard-image based on the obtained standard-image, further comprising
        detecting that an operational irregularity has occurred in at least one of the excitation light and reference-light emitting means, and in response to a detection signal thereof,
        emitting the illuminating-light,
        switching the image obtaining means to a standard-image obtaining mode,
        obtaining the standard-image, and
        displaying the standard-image.

2. A method of displaying a fluorescent-light image comprising
    irradiating a target area with an illuminating light and a excitation light that has been emitted from a excitation light emitting means and guided to said target area, obtaining, by use of a single image obtaining means provided with separate image obtaining portions for obtaining a fluorescent-light image and a standard-image, respectively a fluorescent-light image formed of the fluorescent-light emitted from the target area upon the irradiation thereof by the excitation light and a standard-image formed of the reflected-light reflected from the target area upon the irradiation thereof by the illuminating light, and displaying a fluorescent-light image based on the obtained fluorescent-light image and a standard-image based on the obtained standard-image, further comprising detecting that an operational irregularity has occurred in any one of the image obtaining portions, and in response to a detection signal thereof, emitting the illuminating-light, obtaining, by use of the image obtaining portion that is not operating irregularly, a standard-image formed of the reflected-light reflected form the target area upon irradiation thereof by said illuminating-light, and displaying the standard-image.

3. A method of displaying a fluorescent-light image comprising irradiating a target area with an illuminating light and a excitation light emitted from a excitation light emitting means and a reference-light emitted from a reference-light emitting means and which have been guided to said target area, obtaining, by use of a single image obtaining means provided with separate image obtaining portions for obtaining a fluorescent-light image, a standard-image, and a reflected-light image, respectively, a fluorescent-light image formed of the fluorescent-light emitted from the target area upon the irradiation thereof by the excitation light, a standard-image formed of the reflected-light reflected from the target area upon the irradiation thereof by the illuminating light, and a reflected-light image formed of the reflected-light reflected from the target area upon the irradiation thereof by the reference-light, and displaying a fluorescent-light image based on the obtained fluorescent-light image and the obtained reflected-light image and a standard-image based on the obtained standard-image, further comprising detecting that an operational irregularity has occurred in any one of the image obtaining portions, and in response to a detection signal thereof, emitting the illuminating-light, obtaining, by use of an image obtaining portion that is not operating irregularly, a standard-image formed of the reflected-light reflected form the target area upon irradiation thereof by said illuminating-light, and displaying the standard-image.

4. An apparatus for displaying a fluorescent-light image, comprising excitation light emitting means for emitting a excitation light, illuminating-light emitting means for emitting an illuminating-light, reference-light emitting means for emitting a reference-light, light guiding means for guiding the excitation light, the illuminating-light, and the reference-light to a target area, a single image obtaining means provided with separate image obtaining portions for obtaining a fluorescent-light image formed of the fluorescent-light emitted from the target area upon the irradiation thereof by the excitation light, a standard-image formed of the reflected-light reflected from the target area upon the irradiation thereof by the illuminating light, and a reflected-light image formed of the reflected-light reflected from the target area upon the irradiation thereof by the reference-light, respectively, display means for displaying a fluorescent-light image based on the on the obtained fluorescent-light image and the obtained reflected-light image and a standard-image based on the obtained standard-image, an image display controlling means for controlling the excitation light emitting means, the illuminating-light emitting means, the reference-light emitting means, the image obtaining means, and the display means, further comprising emission output irregularity detecting means for detecting that an operational irregularity has occurred in at least one from among the excitation light emitting means and the reference-light emitting means, and a standard-image display controlling means for causing, in response to a detection signal from said emission output irregularity detecting means, the illuminating-light to be emitted from the illuminating-light emitting means, the image obtaining means to switch to a standard-image obtaining mode, and the display means to switch to the standard-image display mode.

5. An apparatus for displaying a fluorescent-light image, comprising excitation light emitting means for emitting a excitation light, illuminating-light emitting means for emitting an illuminating-light, light guiding means for guiding the excitation light and the illuminating-light to a target area, a single image obtaining means provided with separate image obtaining portions for obtaining a fluorescent-light image formed of the fluorescent-light emitted from the target area upon the irradiation thereof by the excitation light and a standard-image formed of the reflected-light reflected from the target area upon the irradiation thereof by the illuminating light, respectively, display means for displaying a fluorescent-light image based on the on the obtained fluorescent-light image and a standard-image based on the obtained standard-image, an image display controlling means for controlling the excitation light emitting means, the illuminating-light emitting means, the image obtaining means, and the display means, further comprising image-obtainment irregularity detecting means for detecting that an operational irregularity has occurred in any one of the image obtaining portions, and a standard-image display controlling means for causing, in response to a detection signal from said image-obtainment irregularity detecting means, the illuminating-light to be emitted from the illuminating-light emitting means, the image obtaining means to switch to the image obtaining portion that is not operating irregularly, and the display means to switch to the standard-image display mode.

6. An apparatus for displaying a fluorescent-light image, comprising
- excitation light emitting means for emitting a excitation light,
- illuminating-light emitting means for emitting an illuminating-light,
- reference-light emitting means for emitting a reference-light,
- light guiding means for guiding the excitation light, the illuminating-light, and the reference-light to a target area,
- a single image obtaining means provided with separate image obtaining portions for obtaining a fluorescent-light image formed of the fluorescent-light emitted from the target area upon the irradiation thereof by the excitation light, a standard-image formed of the reflected-light reflected from the target area upon the irradiation thereof by the illuminating light, and a reflected-light image formed of the reflected-light reflected from the target area upon the irradiation thereof by the reference-light, respectively,
- display means for displaying a fluorescent-light image based on the on the obtained fluorescent-light image and the obtained reflected-light image and a standard-image based on the obtained standard-image,
- an image display controlling means for controlling the excitation light emitting means, the illuminating-light emitting means, the reference-light emitting means, the image obtaining means, and the display means, further comprising
  - image-obtainment irregularity detecting means for detecting that an operational irregularity has occurred in any one of the image obtaining portions, and
  - a standard-image display controlling means for causing, in response to a detection signal from said image-obtainment irregularity detecting means, the illuminating-light to be emitted from the illuminating-light emitting means, the image obtaining means to switch to an image obtaining portion that is not operating irregularly, and the display means to switch to the standard-image display mode.

7. An apparatus for displaying a fluorescent-light image, comprising
- excitation light emitting means for emitting a excitation light,
- illuminating-light emitting means for emitting an illuminating-light,
- light guiding means for guiding the excitation light and the illuminating-light to a target area,
- a single image obtaining means provided with separate image obtaining portions for obtaining a fluorescent-light image formed of the fluorescent-light emitted from the target area upon the irradiation thereof by the excitation light and a standard-image formed of the reflected-light reflected from the target area upon the irradiation thereof by the illuminating light, respectively,
- display means for displaying a fluorescent-light image based on the on the obtained fluorescent-light image and a standard-image based on the obtained standard-image,
- an image display controlling means for controlling the excitation light emitting means, the illuminating-light emitting means, the image obtaining means, and the display means,
  - a excitation light emission control line, an illuminating-light emission control line, an image obtainment control line, and a display control line, for electrically connecting the excitation light emitting means, the illuminating light-emitting means, the image obtaining means, and the display means, respectively, to the image display controlling means, wherein
  - the illuminating-light means emits the illuminating-light in response to the control signal of the illuminating-light emission control line being in the OFF state,
  - the image obtaining means switches to a standard-image obtaining mode in response to the control signal of the image obtainment control line being in the OFF state,
  - the display means switches to the standard-image obtaining mode in response to the control signal of the display control line being in the OFF state, further comprising
    - a disconnection detecting means for detecting that at least one control line from among the illuminating-light emission control line, the image obtainment control line, and the display control line is disconnected, and
    - a standard-image display controlling means for causing, in response to a detection signal from said disconnection detecting means, the control signal of the control line of from among the illuminating-light emission control line, the image obtainment emission control line, and the display control line that have not been disconnected to be in the OFF state.

8. An apparatus for displaying a fluorescent-light image, comprising
- excitation light emitting means for emitting a excitation light,
- illuminating-light emitting means for emitting an illuminating-light,
- reference-light emitting means for emitting a reference-light,
- light guiding means for guiding the excitation light, the illuminating-light, and the reference-light to a target area,
- a single image obtaining means provided with separate image obtaining portions for obtaining a fluorescent-light image formed of the fluorescent-light emitted from the target area upon the irradiation thereof by the excitation light, a standard-image formed of the reflected-light reflected from the target area upon the irradiation thereof by the illuminating light, and a reflected-light image formed of the reflected-light reflected from the target area upon the irradiation thereof by the reference-light, respectively,
- display means for displaying a fluorescent-light image based on the on the obtained fluorescent-light image and the obtained reflected-light image and a standard-image based on the obtained standard-image,
- an image display controlling means for controlling the excitation light emitting means, the illuminating-light emitting means, the reference-light emitting means, the image obtaining means, and the display means, further comprising
  - a excitation light emission control line, an illuminating-light emission control line, an image obtainment control line, and a display control line, for electrically connecting the excitation light emitting means, the illuminating light-emitting means, the image obtaining means, and the display means, respectively, to the image display controlling means, wherein the illuminating-light means emits the illuminating-light in response to the control signal of the illuminating-light emission control line being in the OFF state, the image obtaining means switches to a standard-image obtaining mode in response to the control signal of the image obtainment control line being in the OFF state, the display means switches to the standard-image obtaining mode in response to the control signal of the display control line being in the OFF state, further comprising a disconnection detecting means for detecting that at least one control line from among the illuminating-light emission control line, the image obtainment control line, and the display control line is disconnected, and a standard-image display controlling means for causing, in response to a detection signal from said disconnection detecting means, the control signal of the control line of from among the illuminating-light emission control line, the image obtainment emission control line, and the display control line that have not been short-circuited to be in the OFF state.

9. An apparatus for displaying a fluorescent-light image as defined in claim 4, 5, 6, 7, or 8, further comprising input means for causing the illuminating-light to be emitted, the image obtaining means to be switched to the standard-image obtaining mode, and the display means to be switched to the standard-image displaying mode when an operational irregularity occurs in the image display controlling means.

10. An apparatus for displaying a fluorescent-light image as defined in claim 9, wherein the display means is provided with a single display apparatus that switches between displaying the fluorescent-light image and the standard-image.

11. An apparatus for displaying a fluorescent-light image as defined in claim 9, the display means is provided with two display apparatuses that display a fluorescent-light image and a standard-image, respectively.

12. An apparatus for displaying a fluorescent-light image as defined in claim 4, 5, 6, 7, or 8, wherein the display means comprises a single display apparatus that switches between displaying the fluorescent-light image and the standard-image.

13. An apparatus for displaying a fluorescent-light image as defined in claim 4, 5, 6, 7, or 8, the display means is provided with two display apparatuses that display a fluorescent-light image and a standard-image, respectively.

14. An apparatus for displaying a fluorescent-light image as defined in claim 5, or 6, wherein the display apparatus is provided with two display apparatuses that display a fluorescent-light image and a standard-image, respectively, and in response to the detection signal indicating that an operational irregularity has occurred in any of the image obtaining portions, the display apparatus, from among said two display apparatuses, that had been displaying the image obtained by the image obtaining portion for which an operational irregularity has been detected does not display an image.

15. An apparatus for displaying a fluorescent-light image as defined in claim 5, or 6, wherein the display apparatus is provided with two display apparatuses that display a fluorescent-light image and a standard-image, respectively, and in response to the detection signal indicating that an operational irregularity has occurred in any of the image obtaining portions, the display apparatus, from among said two display apparatuses, that had been displaying the image obtained by the image obtaining portion for which an operational irregularity has been detected displays a freeze-frame image.

16. An apparatus for displaying a fluorescent-light image as defined in claim 5, or 6, wherein the display apparatus is provided with two display apparatuses that display a fluorescent-light image and a standard-image, respectively, and in response to the detection signal indicating that an operational irregularity has occurred in any of the image obtaining portions, the display apparatus, from among said two display apparatuses, that had been displaying the image obtained by the image obtaining portion for which an operational irregularity has been detected displays an message indicating that an operation irregularity has occurred in an image obtaining portion.

17. An apparatus for displaying a fluorescent-light image as defined in claim 4, 5, 6, 7, or 8, wherein the excitation light source is a GaN semiconductor laser.

18. An apparatus for displaying a fluorescent-light image, comprising excitation light emitting means for emitting a excitation light, illuminating-light emitting means for emitting an illuminating-light, light guiding means for guiding the excitation light and the illuminating-light to a target area, a single image obtaining means provided with separate image obtaining portions for obtaining a fluorescent-light image formed of the fluorescent-light emitted from the target area upon the irradiation thereof by the excitation light and a standard-image formed of the reflected-light reflected from the target area upon the irradiation thereof by the illuminating light, respectively, display means for displaying a fluorescent-light image based on the obtained fluorescent-light image and a standard-image based on the obtained standard-image, an image display controlling means for controlling the excitation light emitting means, the illuminating-light emitting means, the image obtaining means, and the display means, further comprising excitation light irregularity detecting means for detecting that an operational irregularity has occurred in the excitation light emitting means, a standard-image display controlling means for causing, in response to a detection signal from said excitation light irregularity detecting means, the illuminating-light to be emitted from the illuminating-light emitting means, the image obtaining means to switch to a standard-image obtaining mode, and the display means to switch to the standard-image display mode, and input means for causing the illuminating-light to be emitted, the image obtaining means to be switched to the standard-image obtaining mode, and the display means to be switched to the standard-image displaying mode when an operational irregularity occurs in the image display controlling means.

19. An apparatus for displaying a fluorescent-light image as defined in claim 18, wherein the display means is provided with a single display apparatus that switches between displaying the fluorescent-light image and the standard-image.

20. An apparatus for displaying a fluorescent-light image as defined in claim 18, wherein the display means is provided with two display apparatuses that display a fluorescent-light image and a standard-image, respectively.

21. An apparatus for displaying a fluorescent-light image, comprising excitation light emitting means for emitting a excitation light, illuminating-light emitting means for emitting an illuminating-light, light guiding means for guiding the excitation light and the illuminating-light to a target area, a single image obtaining means provided with separate image obtaining portions for obtaining a fluorescent-light image formed of the fluorescent-light emitted from the target area upon the irradiation thereof by the excitation light and a standard-image formed of the reflected-light reflected from the target area upon the irradiation thereof by the illuminating light, respectively, display means for displaying a fluorescent-light image based on the obtained fluorescent-light image and a standard-image based on the obtained standard-image, an image display controlling means for controlling the excitation light emitting means, the illuminating-light emitting means, the image obtaining means, and the display means, further comprising excitation light irregularity detecting means for detecting that an operational irregularity has occurred in the excitation light emitting means, and a standard-image display controlling means for causing, in response to a detection signal from said excitation light irregularity detecting means, the illuminating-light to be emitted from the illuminating-light emitting means, the image obtaining means to switch to a standard-image obtaining mode, and the display means to switch to the standard-image display mode, wherein the display means is provided with two display apparatuses that display a fluorescent-light image and a standard-image, respectively.

22. An apparatus for displaying a fluorescent-light image, comprising excitation light emitting means for emitting a excitation light, illuminating-light emitting means for emitting an illuminating-light, light guiding means for guiding the excitation light and the illuminating-light to a target area, a single image obtaining means provided with separate image obtaining portions for obtaining a fluorescent-light image formed of the fluorescent-light emitted from the target area upon the irradiation thereof by the excitation light and a standard-image formed of the reflected-light reflected from the target area upon the irradiation thereof by the illuminating light, respectively, display means for displaying a fluorescent-light image based on the obtained fluorescent-light image and a standard-image based on the obtained standard-image, an image display controlling means for controlling the excitation light emitting means, the illuminating-light emitting means, the image obtaining means, and the display means, further comprising excitation light irregularity detecting means for detecting that an operational irregularity has occurred in the excitation light emitting means, and a standard-image display controlling means for causing, in response to a detection signal from said excitation light regularity detecting means, the illuminating-light to be emitted from the illuminating-light emitting means, the image obtaining means to switch to a standard-image obtaining mode, and the display means to switch to the standard-image display mode, wherein the excitation light source is a GaN semiconductor laser.

* * * * *